United States Patent [19]
Greenberger

[11] Patent Number: 5,883,339
[45] Date of Patent: Mar. 16, 1999

[54] VIBRATION ISOLATION MOUNT FOR A STETHOSCOPE CHESTPIECE, AND METHODS OF USING SAME

[76] Inventor: Hal Greenberger, 182 Laurelwood Dr., Hopedale, Mass. 01747

[21] Appl. No.: 828,249

[22] Filed: Mar. 31, 1997

[51] Int. Cl.$^6$ ............................................. A61B 7/02
[52] U.S. Cl. ............................................. 181/131; 181/137
[58] Field of Search ............................................. 181/131, 137; 381/67; 128/715

[56] References Cited

U.S. PATENT DOCUMENTS

| | | | |
|---|---|---|---|
| 4,458,778 | 7/1984 | Bloom | 181/131 |
| 4,475,619 | 10/1984 | Packard | 181/137 |
| 5,492,129 | 2/1996 | Breenberger | 181/131 |
| 5,578,799 | 11/1996 | Callahan et al. | 181/137 |

*Primary Examiner*—Khanh Dang
*Attorney, Agent, or Firm*—Brian M. Dingman

[57] ABSTRACT

A mechanical system for reducing unwanted vibration of a stethoscope chestpiece, which reduces the signal components of the chestpiece output due to sources of vibration other than internal physiologic processes within the patient's body. The system includes a compliance, a mass, and a mechanical resistance element, which together increase transmission loss of external sources of vibration between their source and the chestpiece transducer. Methods of using such a system are also disclosed.

39 Claims, 11 Drawing Sheets

300

301

302

303

402

403

VIBRATION ISOLATION MOUNT FOR A STETHOSCOPE CHESTPIECE, AND METHODS OF USING SAME

FIELD OF THE INVENTION

This invention relates to the fields of vibration isolation and noise reduction, and in particular relates to all forms of stethoscopes, encompassing passive mechanical devices and electronic amplified devices. The invention is concerned with reducing the signal components of the output of a stethoscope chestpiece due to sources of vibration other than internal physiologic processes within the patient's body.

DESCRIPTION OF PRIOR ART

Traditional passive mechano-acoustic stethoscopes employ a chestpiece, which is designed to transduce the vibrations of a patient's chest wall (or other portions of the body that may be of interest) into air pressure variations. These air pressure variations are then conducted through tubes to ear pieces that fit into the user's ear canals. The chestpiece is able to convert the skin vibrations into air pressure variations by coupling a small air chamber to the skin. This is commonly done using both bell and diaphragm type chestpieces. In the diaphragm type chestpiece, the diaphragm seals an air cavity located behind the diaphragm from the outside environment. The user places the chestpiece on the patient so that the diaphragm is in contact with the patient's skin. In the bell type chestpiece, the air cavity of the bell is sealed from the outside environment when the bell is placed against the skin. In the bell type chestpiece, the skin acts as the diaphragm. For both chestpiece types, when the skin vibrates, it causes the volume of air in the air chamber to change in sympathy with the skin vibration. This in turn causes the air pressure inside the air chamber to vary in sympathy with the skin vibration. These air pressure variations are then conducted through tubes to the user's ears.

All current methods for transducing the skin vibration of a patient (encompassing both passive mechanical and active electronic methods) transduce the skin vibration relative to a frame of reference. In the case of traditional bell and diaphragm type chestpieces, the frame of reference is the chestpiece body. Electronic stethoscopes that use microphones as transducers employ an air chamber in the same manner as described above for passive chestpieces. Skin vibrations relative to the chestpiece body are transduced into air pressure variations within the air chamber. A microphone is placed inside the air chamber to transduce the air pressure variations into an electrical signal. The frame of reference for electronic stethoscopes that use microphones is also the chestpiece body. In the case of other types of sensors (that may sense skin displacement, velocity, or acceleration directly), the frame of reference is usually, but not always, the body of the sensor. In some cases, the frame of reference may be the ground, as is sometimes the case for accelerometer type sensors.

All of the existing methods of transducing skin vibrations currently used in stethoscopes operate by requiring the user's hand to hold the chestpiece in place against the skin. The user applies a force to the chestpiece body, to hold it in place. The force applied, and the increase in effective moving mass of the chestpiece body when held by the user's hand, tends to keep the chestpiece body reasonably well fixed in space (when no external sources of vibration are present). The user adjusts the force applied so that the chestpiece body is held fixed against the patient's skin, while not applying excessive force to the point that the vibration of the patient's skin under the chestpiece body is restricted. In this way, the vibration of the skin relative to the chestpiece body can be transduced.

The quantity that is of interest is the vibration of the skin due only to internal physiologic processes within the patient's body, relative to a frame of reference that is fixed in space, such as the earth. The quantity that is actually transduced, for most chestpiece transduction methods, is the total skin vibration due to all possible vibration sources, relative to the chestpiece body. In the case of an accelerometer type sensor, the total skin vibration may be transduced relative to the earth. Unfortunately, there are many sources of vibrational energy, other than internal physiologic processes within the patient's body, that can affect the actual signal that is transduced.

For example, ambient airborne noise that is present within the environment can cause the skin of the patient to vibrate. The stethoscope chestpiece will transduce this vibration along with the desired vibration due to internal physiologic processes. In a mechano-acoustic stethoscope, the pressure signal conducted to the user's ears will be a combination of pressure variations in the chestpiece air cavity due to the patient's internal physiologic processes, and pressure variations due to vibration of the skin caused by ambient noise. Traditional stethoscopes are not capable of distinguishing between these sources of air pressure variations. This is the primary reason why traditional stethoscopes are not useful in high noise environments. Methods for actively compensating for the corruption of the chestpiece output signal by airborne ambient noise sources are described in the author's previous U.S. Pat. No. 5,492,129, and will not be dealt with further here. However, it should be noted that all sensor types currently available that directly transduce skin vibration suffer from the same problem when airborne noise is present, unless some type of noise cancellation process is employed. This is because the airborne noise source causes the patient's skin to vibrate, and this vibration is what is transduced.

It is also possible for the patient's body to vibrate due to energy conducted through the body from an external source. This can happen, for example, in an ambulance where vibration of the wheels of the ambulance is transmitted through the vehicle suspension to the floor inside the ambulance, then into the gurney and through the gurney into the patient. This vibration can cause the patient's body to move relative to the chestpiece body, which gives rise to a noise signal in the transduced output of the chestpiece. A noise signal will be generated under these conditions for all sensor types, including sensors that are referenced to the ground rather than the sensor body. Vibration conducted through a structure into the patients body causes the patient's body to vibrate relative to the ground, as well as relative to the chestpiece body.

Yet another source of vibration that can affect the system is vibration of the user's hand when the user is holding the chestpiece. In the case of traditional stethoscopes (and electronic stethoscopes that use microphones to transduce the air pressure in an air chamber), vibration of the user's hand results in a variation in the frame of reference used for the transduction of the skin vibration. This gives rise to a signal in the output of the chestpiece sensor that is due to the vibration of the user's hand, not due to internal physiologic processes within the patient's body. In the case of an accelerometer type sensor, vibration of the user's hand does not result in variation of the frame of reference. However, hand vibration does directly cause vibration of the sensor relative to the fixed ground reference. This also results in a signal component in the output of the sensor that is due to the user's hand vibration.

Vibration of the user's hand can result from processes within the user's body, or from vibration sources outside the user's body. Vibration of the hands due to physiologic processes within the user's body are common in the elderly, where an uncontrolled shaking of the hands is often observed. There are many other potential external sources of vibration that can affect the user's hand that one can conceive of. A common situation where such vibration can exist is in patient transport, which has already been mentioned as an external source of vibration of the patient's body.

Another related vibration problem is referred to as handling noise. The movement of the user's hand along the surface of the chestpiece body can set up vibrations directly in the chestpiece body structure. These vibrations can often contain energy at higher frequencies, which are related to structural resonances within the chestpiece body. The slipping of the fingers with respect to the surface of the chestpiece body can excite these resonances. These vibrations affect both traditional mechano-acoustic stethoscopes as well as amplified electronic stethoscopes. The structural vibrations result in relative motion of the chestpiece body with respect to the patient's skin. These vibrations can be large compared to the skin vibrations it is desired to transduce. In addition, in electronic stethoscopes, the structural vibrations of the chestpiece are often directly coupled to the electro-mechanical transducer used, which further increases the level of the problem.

Finally, it is possible for multiple vibration sources to be present simultaneously. For example, it will often be the case during patient transport, that vibration from the wheels of the ambulance will be conducted through one path into the patient's body, and will simultaneously be conducted through a different path to the user's hand. Both the patient's body and the user's hand will be vibrating relative to a fixed reference, and because the transmission paths are different, they will also be vibrating relative to each other. At the same time, the user's hand could also be shaking, and handling noise can be generated as the chestpiece is moved to different locations on the patient's body.

In U.S. Pat. No. 5,539,831, Harley attempts to address some of these vibration issues through the use of an additional sensor. This sensor is designed to be placed on the body to sense vibration of the body that is not due to internal physiologic processes. The output of this sensor is then processed through a complicated adaptive digital system in an attempt to try to cancel the portion of the output signal of the chestpiece sensor that is due to body vibration caused by sources other than internal physiologic processes. The system proposed by Harley is complex, and requires the use of sophisticated electronics to function. Its capability is also limited. The system of Harley cannot reduce the effects of vibration of the user's hand, because his third sensor cannot detect this vibration. The system of Harley also cannot reduce handling noise, for the same reason.

In contrast, the current invention achieves its vibration reduction through purely passive mechanical means. It is quite inexpensive to implement. It is applicable to passive mechano-acoustical stethoscope chestpieces, as well as electronic stethoscope sensors. No electronic signal processing is required. The invention reduces the effects from vibration sources that cause the user's hand to vibrate relative to the patient's skin (whether they arise from processes internal or external to the user's body). These sources of vibration contamination have not been adequately addressed in the prior art. The invention also reduces the effects of vibration caused by handling. Finally, the invention simultaneously reduces the effects of combinations of the above vibration sources.

SUMMARY OF THE INVENTION

This invention relates to the use of stethoscopes in environments where sources of vibration exist other than vibration of the patient's skin due to internal physiologic processes. It is the purpose of the present invention to provide a system that reduces the effects of these undesirable vibration sources on the output signal of a stethoscope chestpiece, while preserving the output signal due to internal physiologic processes. This is accomplished by introducing a mechanical isolation system. The purpose of the isolation system is to increase the transmission loss between the point where the external unwanted vibration energy enters the system, and the portion of the chestpiece assembly responsible for transducing the vibration of the patient's skin. The components of the mechanical isolation system are arranged and chosen so that they divert away or absorb the undesirable vibration energy, in order to minimize the effects of this undesirable vibration energy on the output of the stethoscope chestpiece.

The isolation system in the preferred embodiment consists of a compliant member that has a mechanical compliance, a chestpiece shell element that has a mechanical mass, and mechanical resistance elements that provide damping, where the compliant member is connected between the chestpiece body and the chestpiece shell, and the mechanical resistance elements are placed in the isolation system structure in locations where damping of high frequency structural vibrations can be obtained. The preferred embodiment uses a second order isolation system, where the order of the system is determined by the number of energy storage elements added. Energy storage elements are masses and compliances (which in this case are the chestpiece shell and compliant member). Isolation systems of different orders are also possible.

The preferred embodiment of the vibration isolation mount system of the present invention can be operated in a number of different modes. The different modes of operation will be shown to have different overall behaviors as regards the reduction of the effects of undesired external vibration energy on the chestpiece output signal. The various operating modes differ primarily in how the overall chestpiece assembly with isolation mount system is held against the patient's skin by the user. The operating modes differ in function primarily in the frequency ranges where reduction in the effects of external vibration sources occur, and in the total amount of reduction accomplished in those frequency ranges.

In a first mode of operation (in which the user holds the chestpiece shell, and the shell does not contact the patient's skin), vibration isolation between the chestpiece shell and the chestpiece body occurs for frequencies above the resonance frequencies of the combination of the compliant member mechanical compliance with the chestpiece body mass and with the chestpiece shell mass. It will be shown that vibration transmission from the chestpiece shell to the chestpiece body for the preferred embodiment has a low pass transfer function.

In a second operating mode (in which the user holds the chestpiece body and the chestpiece shell is free to vibrate), the system acts as a resonant absorber over a band of frequencies. The combination of the compliant member compliance and the chestpiece shell mass form a resonant absorber system that absorbs vibration energy of the chestpiece body in the frequency range centered about the resonance frequency of the absorber. Operation in this mode is useful when an external force is applied to the chestpiece body that is centered in a particular frequency range. One situation where this can occur is with an elderly user. It is often the case that the hands of an elderly person have some level of uncontrollable shaking. The absorber can be tuned to the frequency of the hand shaking to absorb the effects of the shaking on the chestpiece output.

In a third operating mode (in which the user holds the chestpiece shell, and the shell is in contact with the patient's skin), the system adds a broadband vibration isolation component between the chestpiece shell and chestpiece body, to the isolation described above for the first mode of operation. This allows the system to provide a level of vibration transmission reduction at frequencies below the system resonances, in addition to the transmission reduction provided above resonance described earlier where a low pass character was obtained.

A compliant member can be described as a mechanical element where the linear displacement of the compliant member is inversely proportional to the mechanical compliance and proportional to the applied force. This relationship is shown below:

$$F = -(1/C)*x,$$

where C is the mechanical compliance, x is the displacement, and F is the force. An equivalent representation can also be used. This equation is shown below.

$$F = -k*X,$$

The above equation can be recognized as the force balance equation for a spring, where k is the spring constant which represents the spring mechanical stiffness. The above two descriptions are equivalent. The mechanical compliance and mechanical stiffness of a spring are reciprocals of each other (k=1/C). The system models developed represent spring elements as compliances, rather than stiffness, because of mathematical convenience. The terms compliant member or compliant element will be used throughout this disclosure to refer to elements where the applied force is proportional to displacement. These elements could also be referred to as springs, stiffness elements, or stiffness members without any loss of generality.

The behavior of the isolation system will be shown to also depend on the masses of different components of the system. A mass can be described as a mechanical element where the linear acceleration of the mass is proportional to the mass and the applied force. This is shown in the following equation:

$$F = m*a, \qquad (2)$$

where m is the mass and a is the acceleration of the mass.

In the preferred embodiment, (for operation in the first and third modes), the transmission of vibration from the chestpiece shell to the chestpiece body through the isolation mount system will have a second order low pass character, where the cut off frequency of the low pass filter function is the resonance frequency of the chestpiece shell mass combined with the mass of the user's hand and arm, and the compliant member compliance. The complete transfer function from chestpiece shell to the chestpiece air chamber pressure output for a mechano-acoustic stethoscope with the preferred embodiment vibration isolation mount will be shown to have a fourth order low pass character, where the additional poles of the transfer function are primarily determined by the chestpiece body mass, the system damping, and the combination of the compliance of the chestpiece air chamber and skin compliance.

The mechanical isolation elements added to the new stethoscope system of the current invention also affect the chestpiece output signal due to desired internal physiologic processes when the new stethoscope system is used in its first and third operating modes. The resonance between the compliant member compliance and the chestpiece body mass have a direct influence. These elements introduce a transfer function between the desired physiologic sources and the chestpiece output that has approximately a second order high pass shelving form. Manipulation of the transition frequencies of this shelving high pass filter will be of value in some circumstances.

The transition frequency locations and the magnitude response of the transfer function in the vicinity of these frequencies can be changed by adjusting the mechanical compliance of the compliant member, the mass of the chestpiece body, and the mechanical resistance of the mechanical resistance elements. If, for example, it is desired to raise the transition frequencies in order to reduce the level of cardiac sounds in the chestpiece output (where cardiac sounds are made up primarily of low frequency information), the mechanical compliance of the compliant member can be reduced, or the mass of the chestpiece body can be reduced. Similarly, the transition frequencies can be lowered by increasing the mechanical compliance of the compliant member and/or increasing the mass of the chestpiece body. Adjustment of the amount of mechanical resistance will affect the response of the system in the vicinity of the transition frequencies.

It is possible for the mechanical compliance of the complaint member to be made adjustable by the user. The invention is not limited in the method used for constructing a variable compliance element. It is also possible for the mass of the chestpiece body and/or the chestpiece shell to be made adjustable by the user. Small weights can be added or removed from a chestpiece body or shell assembly to adjust the respective masses. An explicit method for constructing a variable mass system is not shown. It is assumed that a person skilled in the art will be capable of easily creating such an assembly.

The user adjustable compliant element and user adjustable mass element can be used to vary the tuning frequency of the resonant absorption that is obtained when the new stethoscope system is used in its second intended operating mode. The user adjustable elements can also be used to vary the frequency response of the transduced desired body sounds by varying the high pass shelving response transition frequencies that were mentioned earlier.

The travel of the shell assembly relative to the chestpiece body is also designed, along with the mechanical compliance of the compliant member, so that the static force applied by the compliant member to hold the chestpiece body against the patient's skin is sufficient to hold the chestpiece in place, and to allow accurate transduction of the patient's skin vibration.

The preferred embodiment uses mechanical resistance elements, which provide a damping function. The mechanical resistance elements are shown placed in between the chestpiece shell and the chestpiece body, along with the compliant member. The preferred embodiment shows resistance elements placed in the isolation mount structure where the compliant member attaches to the chestpiece body. Other methods of applying mechanical resistance elements can also be used with success, and the invention is not limited in where elements are applied to the structure to provide damping of vibration energy. Mechanical resistance elements may be placed along the entire length of the compliant element, they may be located where the compliant element attaches to the chestpiece shell or attaches to the chestpiece body, or they can be attached to the chestpiece shell and chestpiece body directly. Combinations of the above mechanical resistance elements can also be used effectively.

The mechanical resistance elements have two functions. The first is to damp high frequency resonances in the mechanical structure that consists of the chestpiece shell, chestpiece body, and compliant member. The presence of un-damped structural resonances would allow high frequency vibration energy that was present at system structural resonance frequencies to be transmitted from the chestpiece shell to the chestpiece body without significant attenuation. The presence of un-damped high frequency structural resonances would defeat the effect of the vibration isolation system at those structural resonance frequencies. The addition of damping is an effective method of increasing the transmission loss at high frequencies in an isolation mount system. High frequency vibration energy often results from handling of the chestpiece structure. The addition of mechanical resistance elements, therefore, reduces handling noise.

The second function of the mechanical resistance elements is to control the behavior of the isolation system at the various fundamental lumped element resonance frequencies of interest.

A mechanical resistance element can be described as a mechanical element where the linear velocity of the mechanical resistance is proportional to the mechanical resistance and the applied force. This is represented by the equation:

$$F = u*r, \qquad (3)$$

where u is the linear velocity and r is the mechanical resistance. Resistance elements do not provide energy storage. Resistance elements model energy dissipation. A mechanical resistance element represents the conversion of mechanical motion into heat.

One method of creating a mechanical resistance is to use an elastomeric material (a low durometer polymeric material). In the case of the preferred embodiment, one side of the elastomer is attached to the compliant member and one side is attached to the chestpiece body. Relative motion of the compliant member with respect to the chestpiece body will cause a deformation of the elastomer. This deformation causes internal stress within and friction between the polymer chains contained in the elastomer structure. The internal stresses and friction cause some of the input energy to be converted into heat. The amount of energy that is transformed into heat is directly proportional to the effective mechanical resistance of the elastomer.

In other embodiments, higher order vibration isolation systems can be constructed to provide additional vibration isolation between external vibration sources and the chestpiece body. These higher order systems consist of adding additional mass, compliance, and resistance elements, that can be placed in the system in various ways, to further reduce the vibration transmission from these external vibration sources to the chestpiece body. Higher order systems are capable of increased vibration isolation at higher frequencies, but possess a more complex behavior at lower frequencies. Higher order systems also possess a more complex physical structure and will be higher in cost than the preferred embodiments. Although higher order isolation systems are not explicitly shown here, the invention is not limited in the order of the isolation system used.

It will be useful to have the ability to defeat the operation of the isolation mount, for situations where there are no significant sources of vibration present other than the internal physiologic processes within the patient's body. This feature can be accomplished by providing a method of clamping the chestpiece shell to the chestpiece body. One method for accomplishing this includes a magnet, in either the chestpiece shell or chestpiece body, that can be used to clamp the shell and body together when desired. Other methods of clamping the shell and body together (such as mechanical clasps, snaps, etc.) are also possible. The invention is not limited in the method used to accomplish this function.

It is possible to design an isolation mount system that can be applied to existing stethoscopes. In this case, all that is required is a clamping mechanism that will connect the compliant element to the existing chestpiece body. For example, the resistance element in FIG. 2 below could be slipped onto and off of the existing chestpiece body. It may be possible to design a universal clamping mechanism that can fit a number of different stethoscopes. In other cases, a clamping mechanism may be designed for a specific stethoscope chestpiece. A specific embodiment of a clamping mechanism is not explicitly shown. It is assumed that those skilled in the art will be capable of fashioning such a device easily.

It is an object of this invention to provide a completely mechanical vibration reduction isolation mounting system for a stethoscope chestpiece that reduces the effects of vibration sources external to the patient's body on the output signal of the chestpiece sensor.

It is a further object of this invention to provide an isolation mounting system for a stethoscope chestpiece that reduces the vibration transmission from the user's hand to the stethoscope chestpiece body.

It is a further object of this invention to provide an isolation mounting system that can be applied to an existing stethoscope to reduce the effects of vibration sources external to the patient's body on the output signal of the chestpiece sensor.

It is a further object of this invention to provide a chest piece isolation mounting method that is applicable to all forms of stethoscope chestpieces, including traditional passive mechano-acoustic devices and electronic devices.

It is a further object of this invention to provide an isolation mounting system for a stethoscope chestpiece that reduces the effects due to handling noise on the output signal of the chestpiece sensor.

It is a further object of this invention to provide a method by which the isolation mounting system can be bypassed by the user, for cases where there are no significant sources of vibration present (other than vibration due to internal physiologic processes within the patient's body).

It is a further object of this invention to provide a system that applies a filter function to the chestpiece output that reduces the level of low frequency desired signal transduced by the chestpiece, to improve audibility of higher frequency vibrations.

It is a further object of this invention to provide a system that applies a filter function to the chestpiece output that reduces the level of low frequency desired body sound signal transduced by the chestpiece, where the frequency range where reduction occurs can be varied by the user.

It is a further object of this invention to provide an isolation mounting system that uses a resonant absorber that reduces the effects of external vibration sources on the chestpiece output over a band of frequencies.

It is a further object of this invention to provide an isolation mounting system that uses a resonant absorber that reduces the effects of external vibration sources on the chestpiece output over a band of frequencies, where the frequency band of vibration absorption can be varied by the user.

It is a further object of this invention to provide an isolation mounting system that provides a broadband reduction of the effects of external vibration sources on the chestpiece output over its entire usable frequency range.

DETAILED DESCRIPTION OF THE PREFERRED EMBODIMENTS

Figure 1:
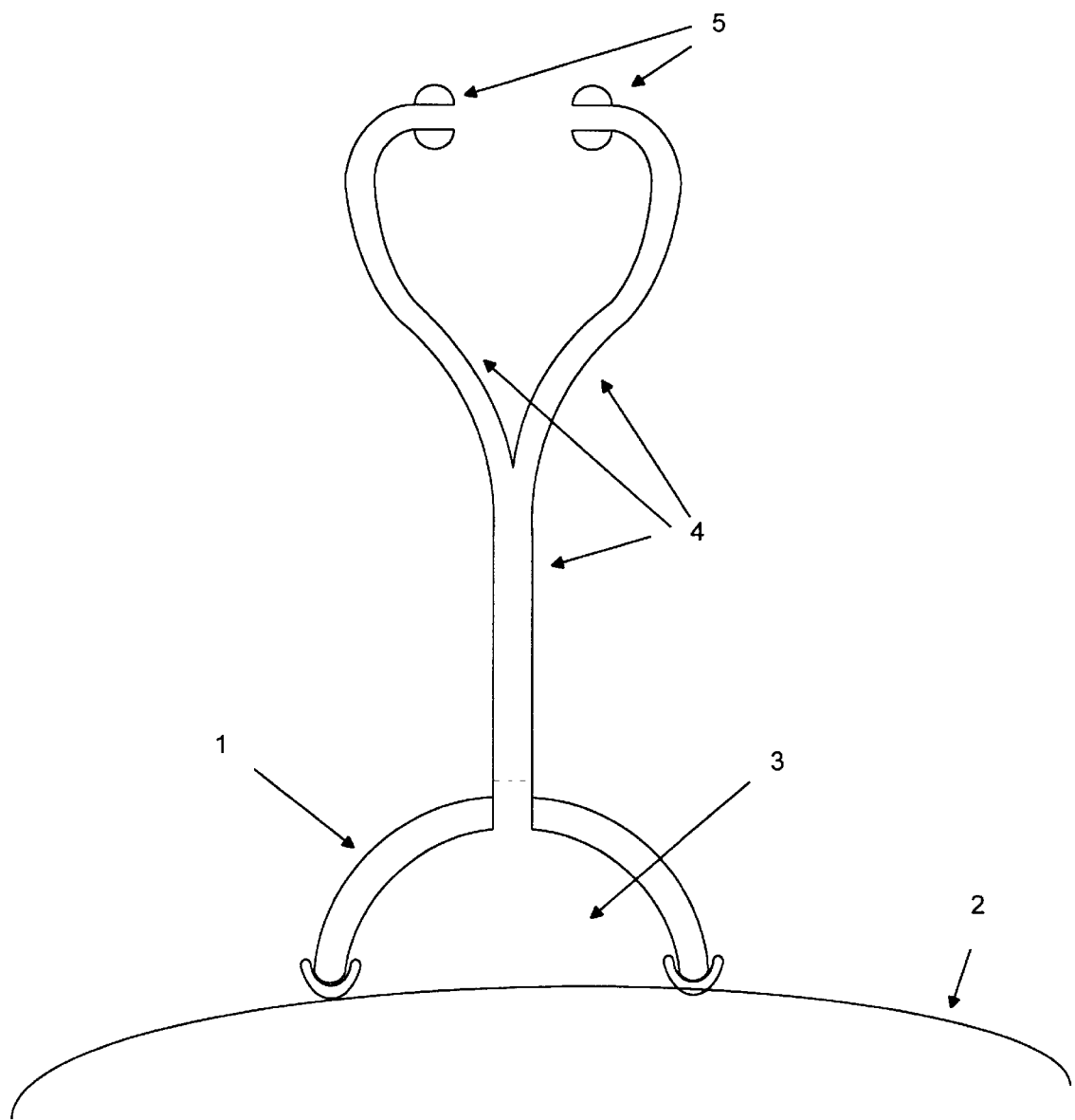
FIG. 1 is a schematic diagram of the principal components of a traditional passive mechano-acoustic stethoscope.

FIG. 1 shows a schematic representation of a traditional stethoscope. Chestpiece 1 is placed against the skin of the patient 2. Vibration of patient's skin 2 causes the air pressure in chamber 3 of chest piece 1, which is the vibration transducer means in a traditional mechano-acoustic stethoscope such as this, to alternate in sympathy with the skin vibration. The pressure variation in chamber 3 is conducted through tubes 4 that connect to the stethoscope ear pieces 5. This is the transduction method used in mechano-acoustic stethoscopes to transduce skin vibrations into acoustic pressure variations which are heard by the user. It is intended that ear pieces 5 are placed in the users ears, and provide an air tight seal to the user's ear canal.

The user holds the chestpiece 1 in place against the patient's skin 2. The system works well as long as the only movement of chestpiece 1 relative to patient's skin 2 is due to internal physiologic processes within the patient's body. Any motion of chestpiece 1 relative to patient's skin 2 that is not a result of vibration due to physiologic processes within the patient's body will cause an air pressure variation in chamber 3 that is not desired. The mechano-acoustic stethoscope is not able to distinguish between air pressure variations in chamber 3 due to internal physiologic processes, and air chamber pressure variations due to the motion of chestpiece 1 relative to patient's skin 2 from other causes. Although FIG. 1 shows a mechano-acoustic stethoscope with a bell type chestpiece body, it is for convenience only. Any type of chestpiece sensor is contemplated herein, as such will generate unwanted signals if there is motion of the sensor relative to the patient's skin that is not due to internal physiologic processes within the patient's body.

Also, any type of chestpiece body is contemplated herein, where the chestpiece body supports the means for transducing skin vibration.

Figure 3B:
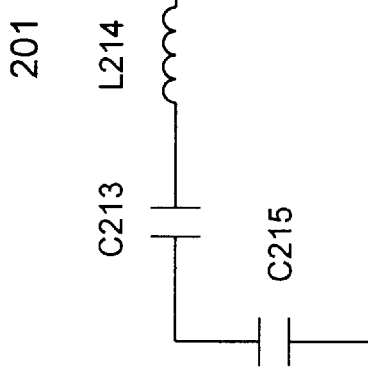
FIG. 3b shows a model of the system in FIG. 3a, where the user holds the chestpiece body at zero velocity.
Figure 3D:
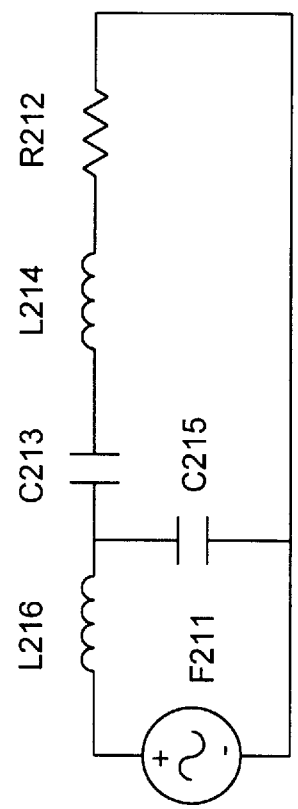
FIG. 3d shows the system of FIG. 3a where only external forces applied to the chestpiece body are considered.
Figure 3A:
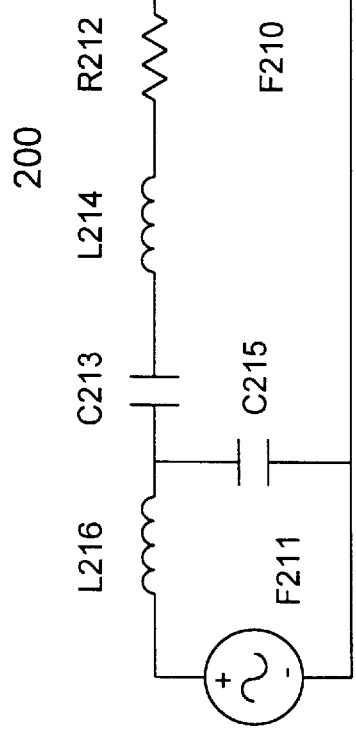
FIG. 3a is an electrical circuit model that represents the behavior of a traditional stethoscope system.

An analogous electrical circuit model for the operation of a traditional stethoscope chestpiece is given in FIG. 3a. Circuit 200 represents the traditional stethoscope system in the mechanical domain. In this analogy, force is analogous to voltage and velocity is analogous to current. This analogy is used throughout for all electrical circuit models shown. Force source 210 represents forces generated by physiologic processes occurring inside the patient's body. Force source 211 represents external forces applied directly to the chestpiece body (such as by the user's hand). Resistor 212 represents the mechanical resistance of the patient's internal tissues and skin. Capacitor 213 represents the mechanical compliance of the patient's internal tissues and skin. Inductor 214 represents the mechanical mass of the patient's internal tissues and skin. The series resonant circuit model for the patient's internal tissues and skin given here is an approximation to the actual mechanical impedance of the body, but it has been found to be an accurate representation of the behavior of the body in the frequency range of interest.

Inductor 216 represents the mechanical mass of the chestpiece body. Inductor 216 also includes the effective mass of the user's hand and arm when the user is holding the chestpiece body. Capacitor 215 represents the equivalent mechanical compliance of air chamber 3 of chestpiece body 1. The voltage across capacitor 215 represents the force applied to the equivalent mechanical compliance of air chamber 3, and is the primary variable of interest. This force is proportional to the air pressure developed in the air cavity, where the constant of proportionality is determined by the area of the chestpiece opening that is coupled to patient's skin 2. Mechanical and acoustical elements are related to each other though the following equations:

$$P=F/S,$$

$$U=u*S$$

$$F=u*Z_m$$

$$P=U*Z_a$$

$$Z_m=S^2*Z_a,$$

where

P is acoustic pressure, F is mechanical force, S is the area of the chestpiece opening, U is the acoustic volume velocity, u is the mechanical velocity, $Z_m$ is the mechanical impedance, and $Z_a$ is the acoustical impedance. $Z_m$ and $Z_a$ for a compliance can be written as:

$$Z_m=1/(C_m*s)$$

$$Z_a=1/(C_a*s),$$

where $C_m$ is the mechanical compliance, $C_a$ is the acoustical compliance, and s is the complex frequency variable. $C_a$ is calculated as follows:

$$C_A=V/(\rho_o*c^2),$$

where

V is the volume of the chestpiece air cavity, $\rho_o$ is the density of air (1.18 kg/m$^3$), and c is the speed of sound in air (345 m/s). The relationship between the equivalent mechanical compliance and the acoustical compliance of the chestpiece air cavity can be shown to be:

$$C_m=C_a/S^2$$

Circuit 201 in FIG. 3b shows the electric circuit model for an ideal case where the chestpiece is held against the patient's skin at zero velocity. The condition of zero velocity implies that the current through inductor 216 is equal to zero. The circuit branch containing inductor 216 is an open circuit. In this ideal case, it can be seen that the voltage across capacitor 215 is solely due to internal force source 210. It can also be seen that the voltage across capacitor 215 will have a second order low pass character. This implies that the pressure developed in the chestpiece air chamber due to internal physiologic processes will have a second order low pass character as a function of frequency.

Figure 3C:
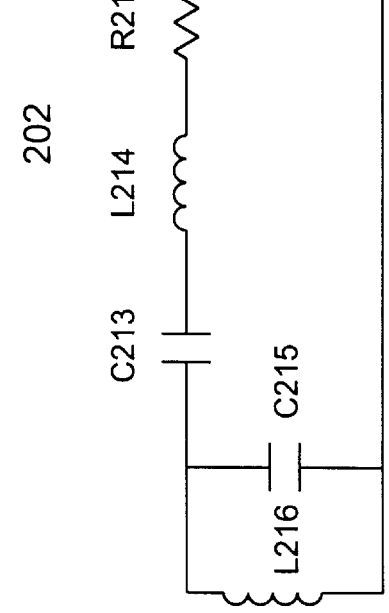
FIG. 3c shows the system of FIG. 3a where only vibration due to physiologic processes within the patient's body are considered.

Circuit 202 in FIG. 3c shows the case where only forces generated by internal physiologic sources are considered. This model is obtained from the model of FIG. 3a using the principal of superposition. It can be seen here that if inductor 216 can be made sufficiently large, its effects in the audible frequency range on the output of the chestpiece due to internal physiologic sources will be minimized. Inductor 216, in this case, includes the effective mass of the user's hand and arm. This implies that the total mass represented by inductor 216 will be large, which is what is desired.

Circuit 203 in FIG. 3d shows the model where only external force source 211 is active. This model is obtained from the model of FIG. 3a using the principal of superposition. This model can be used to determine the pressure response of the stethoscope chestpiece output due to forces directly applied to the chestpiece body (through the user's hand). It can be seen that the pressure response generated in the chestpiece air chamber due to force source 211 will have a second order low pass character (if one ignores the effect of the mechanical load of the patient's body). The corner frequency of this response will be approximately at the resonance frequency determined by combined mass of the chestpiece body and the user's hand and arm, and the equivalent mechanical compliance of the chestpiece air chamber. In general, the frequency range where pressure can occur in the chestpiece air cavity due to external forces applied to the chestpiece body, and the frequency range where pressure can occur in the chestpiece air cavity due to forces generated by internal physiologic processes within the patient's body, will have significant overlap. This is the primary problem that the current invention addresses.

It should be noted that this situation occurs in the outputs of all other known types of chestpiece sensors. It is not confined to the use of traditional chestpieces where an air volume coupled to the patient's skin is used to transduce skin vibration into an acoustic pressure. Electronic sensors that sense the vibration of the skin directly with respect to some fixed frame of reference (where displacement, velocity, or acceleration is sensed) will transduce signals due to both internal physiologic processes and external forces, and the frequency ranges of these signals will have significant overlap. Electronic vibration sensors will have the same problem as the mechano-acoustic transduction system used in traditional stethoscopes.

The goal of the present invention is to develop a system where a chestpiece sensor can be held against the patient's skin to transduce the vibration of the patient's skin due to internal physiologic processes, while minimizing the transduction of vibration sources other than the internal physiologic processes. This goal is accomplished by adding a mechanical isolation system to the stethoscope chestpiece assembly. The components of the mechanical isolation system are arranged and chosen so that they divert away or absorb the undesirable vibration energy, in order to minimize its effects on the output of the stethoscope chestpiece.

Figure 2A:
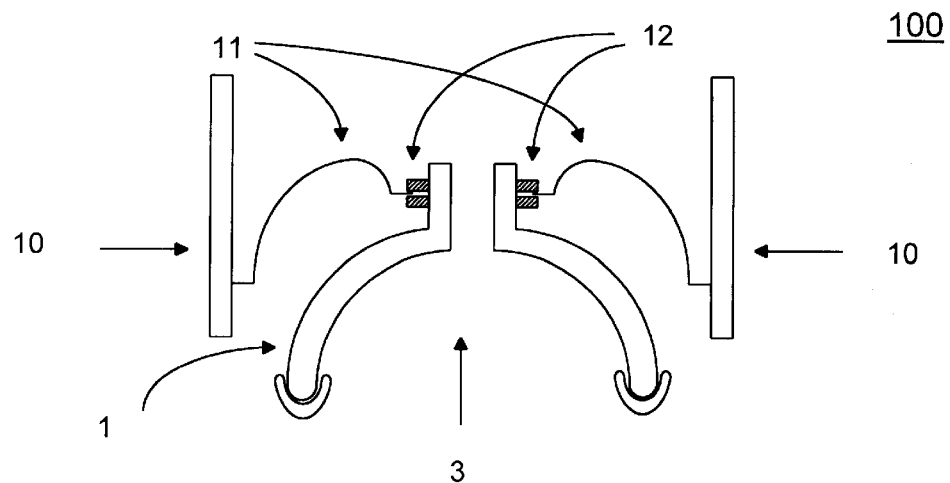
FIG. 2a shows a cross section representation of a preferred embodiment of an isolation mounting system for a stethoscope chest piece according to this invention, where the assembly is shown located in free space. The isolation mounting elements are shown in a schematic representation.
Figure 2B:
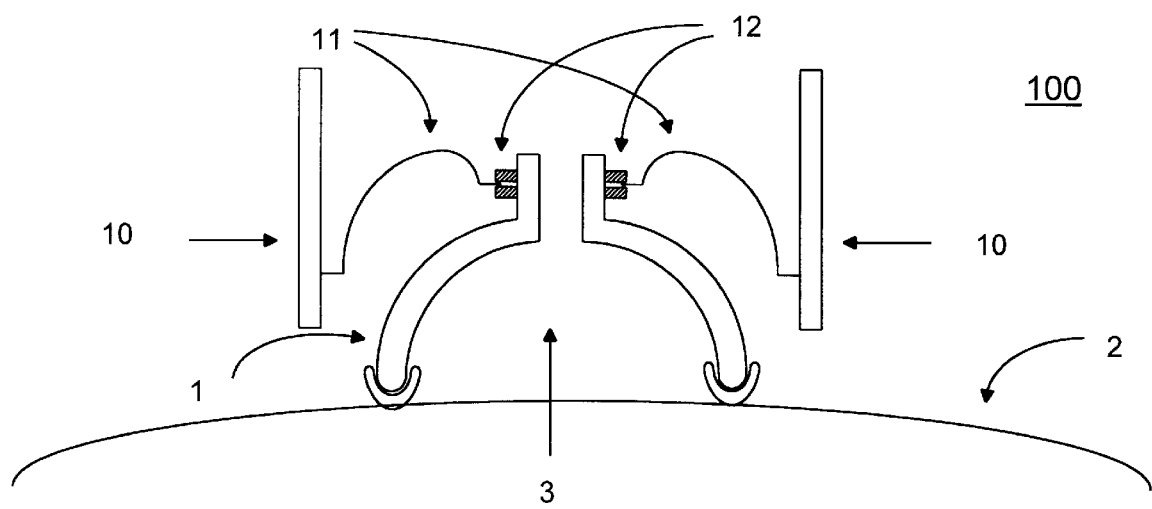
FIG. 2b shows a cross section representation of the embodiment of FIG. 2a operating in its first and second operating modes of this invention, where the chestpiece body is in contact with the patient's skin, but the shell is not in contact with the patient's skin. The user holds the chestpiece shell in the first mode of operation, and the user holds the chestpiece body in the second mode of operation. The isolation mounting elements are shown in a schematic representation.
Figure 2C:
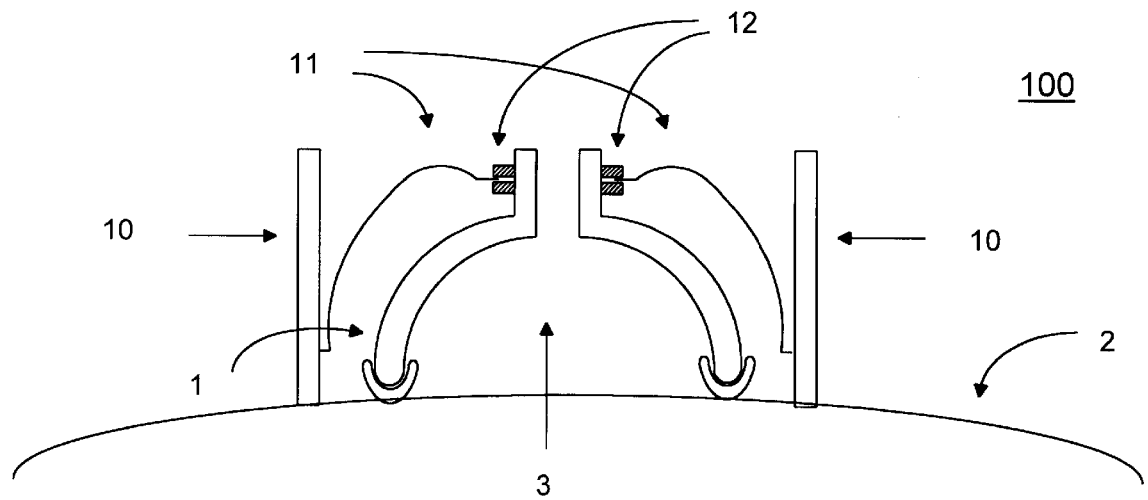
FIG. 2c shows a cross section representation the embodiment of FIG. 2a operating in its third operating mode of this invention, where the chestpiece body is in contact with the patient's skin, and the chestpiece shell is also in contact with patient's skin. The user holds the chestpiece shell. The isolation mounting elements are shown in a schematic representation.

A section view of a preferred embodiment of such an invention is shown in various operating modes in FIGS. 2a–c. Chestpiece assembly 100 consists of outer chestpiece shell 10, compliant member 11, mechanical resistance elements 12, and chestpiece body 1. FIG. 2a shows chestpiece assembly 100 with the assembly located in free space away from the patient's body, where there is no loading of the compliant member present. One end of compliant element 11 is shown attached to the external mass represented by chestpiece shell 10. The other end of compliant member 11 is attached to chestpiece body 1. Mechanical resistance elements are shown attached to compliant member 11 at the location where compliant member 11 attaches to chestpiece body 1.

A vertical offset is shown between chestpiece shell 10 and chestpiece body 1. This is by design. In the first and third intended operating modes of the new embodiment stethoscope chestpiece, the user picks up chestpiece assembly 100 by grasping chestpiece shell 10. When the assembly is placed against patient's skin 2, chestpiece body 1 contacts patient's skin 2 first. The system is designed so that chestpiece body contacts the patient's skin while chestpiece shell 10 can either be held in free space away from the patient's skin, or can rest against the patient's skin by sufficiently compressing compliant member 11. In the second operating mode, the user holds chestpiece body 1 directly against the patient's skin, and chestpiece shell 10 is spaced away from the patient's skin and is free to move.

The compliance of compliant member 11 is chosen for the first and third modes so that it provides sufficient force to hold the chestpiece body in place against the patient's skin. The compliance of compliant member 11 is chosen for the second operating mode so that it resonates with the chestpiece shell mass at a desired frequency.

FIG. 2b shows chestpiece assembly 100 used in its first and second intended modes of operation, where chestpiece body 1 is placed against patient's skin 2, but chestpiece shell 10 is not in contact with patient's skin 2. In the first intended operating mode, the user holds chestpiece shell 10. In the second operating mode, the user holds chestpiece body 1, and chestpiece shell 10 is allowed to vibrate in free space. FIG. 2c shows chestpiece assembly 100 operating in its third intended mode, where chestpiece body 1 and chestpiece shell 10 are both in contact with patient's skin 2. The user holds chestpiece shell 10 in this third operating mode. The user applies force to chestpiece shell 10 that places a sufficient load on compliant member 11 to compress it until chestpiece shell 10 contacts patient's skin 2.

Figure 2D:
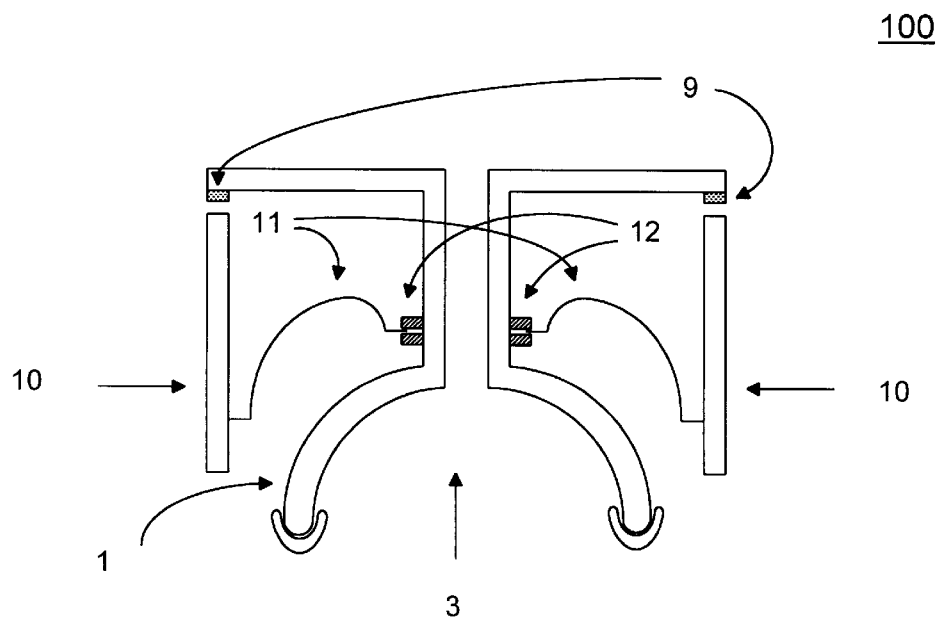
FIG. 2d shows a cross section representation of the embodiment shown in FIG. 2a, where changes have been made that add a clamping mechanism which can be used to affix the chestpiece shell to the chestpiece body.

FIG. 2d shows a chestpiece assembly where a clamping mechanism is provided that allows the chestpiece shell to be fixed to the chestpiece body. This construction is useful for situations when there are no external sources of vibration present. The system of FIG. 2d will behave identically to a traditional stethoscope system. The system of FIG. 2d shows the use of magnet 9 as a clamping mechanism. This is not the only method that can be used to fix the chestpiece shell to the chestpiece body. Mechanical clasps, snaps, etc. can also be used. The invention is not limited in the manner in which the clamping mechanism is realized.

FIGS. 2a–d show element 10 as a shell that surrounds the chestpiece. This construction geometry is not required for proper operation of the present invention. Element 10 provides two functions in the present invention. First, it acts as a mass element. There are no constraints on the geometry of the mass element used. It can be a shell that surrounds the chestpiece body, or it can be a block of arbitrary shape that has a mass, which can be located in various positions with respect to the chestpiece body. The primary requirements of the mass element are that it be connected to the chestpiece body through a compliant element, and that the mass element be free to move in at least the axial direction normal to the surface of the patient's skin.

The second function of element 10 is to provide a surface that the user can hold. This surface can be a shell that completely surrounds the chestpiece, but this is not required. It is sufficient for the mass to have a surface that can be held by the user, that partially or fully surrounds the chestpiece body, for operation in the first and third intended modes. The mass element does not need to be held by the user for operation in the second intended mode. The surface of the mass element must be able to be placed in contact with the patient's skin if operation in the third intended mode is desired. A shell construction is shown for element 10 because it is convenient. The invention is not limited in the geometry chosen for the external mass element used.

The isolation mounting system of the present invention can be designed to be an integral part of the overall stethoscope system. In these designs, the mass of the chestpiece body and acoustic compliance of the chestpiece air cavity (determined by the cavity volume) are under the control of the designer. It is also possible to design an isolation mounting system that is affixed to an already existing stethoscope. In this case, the configuration of the chestpiece body will already be set. It is still possible to design an effective isolation mount where only the mechanical compliance of the compliant element and the mass of the chestpiece shell can be manipulated. The only additional design complexity for such systems is the design of the clamping mechanism that attaches the isolation mount components to the existing stethoscope. It may be possible to design a universal clamping mechanism that fits most existing stethoscopes. It is assumed that the design of such a clamping mechanism is straightforward, and can easily be accomplished by someone skilled in the art. The invention is not limited in the method used to construct such a clamping mechanism.

FIGS. 4a–d show electrical circuit analogous models for the preferred embodiment operating in its first mode. In FIGS. 4a–d, elements 310 through 316 are the same as elements 210 through 216 shown in FIGS. 3a–d, except for inductor 316. Inductor 316 in FIGS. 4a–d only represents the mass of chestpiece body 1 (it does not include the mass of the hand and arm of the user). In addition, 3 new elements appear in FIGS. 4a–d. Capacitor 318 represents the mechanical compliance of compliant member 11 that connects chestpiece shell 10 to chestpiece body 1, resistor 317 represents mechanical resistance elements 12 (which are shown applied to one end of compliant member 11 in FIGS. 2a–d) and inductor 319 represents the combination of the mechanical mass of chestpiece shell 10 and the mechanical mass of the user's hand and arm when the user is holding the chestpiece shell.

Figure 4A:
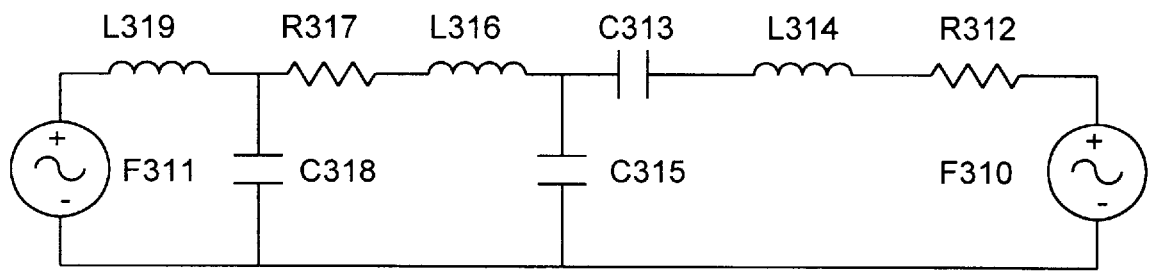
FIG. 4a is an electrical circuit model that represents the behavior of the preferred embodiment stethoscope chestpiece with mechanical isolation mount system according to this invention operated in its first mode, where the user holds the chestpiece shell, and the shell is in free space.

Circuit 300 in FIG. 4a gives the complete model for the preferred embodiment operating in its first operating mode, which is shown in FIG. 2b. In the first operating mode, the user holds chestpiece shell 10 so that chestpiece body 1 is in contact with patient's skin 2, but chestpiece shell 10 is not in contact with patient's skin 2. The compliance of compliant member 11, the combined mass of chestpiece shell 10 and the user's hand and arm, along with the mass of chestpiece body 1 form the primary vibration isolation system. The compliance and masses act as a low pass filter for vibration energy transmission from chestpiece shell 10 (which the user is holding) to chestpiece body 1. This is easily seen in circuit 300 in FIG. 4a and circuit 303 in FIG. 4d. Inductor 319 and capacitor 318 form a low pass filter function from external force source 311 to forces acting on the chestpiece body. Above the cutoff frequency of the low pass filter described above, the force transmitted from chestpiece shell to chestpiece body 1 decreases at the approximate rate of 12 dB per octave. This should be compared to the traditional chestpiece system model shown in FIG. 3a, where external force source 211 was directly coupled to chestpiece body 1 (the user holds the chestpiece directly).

Figure 4B:
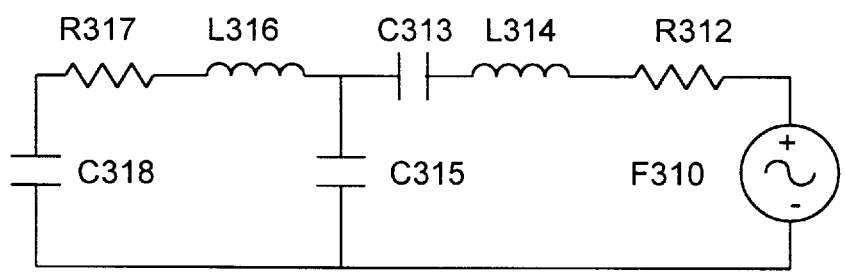
FIG. 4b shows a model of the system in FIG. 4a, where the user holds the chestpiece shell in free space at zero velocity.

Circuit 301 in FIG. 4b shows the model of the preferred embodiment system operated in its first mode, where the user holds the chestpiece shell at zero velocity. Here it can be seen that an additional series resonance exists between capacitor 318 and inductor 316 (and resistance element 317), as compared to the case modeled in FIG. 3b where a traditional stethoscope chestpiece was held at zero velocity. The complete effect of the additional elements on the chestpiece output due to internal physiologic sources is difficult to predict, as there can be numerous interactions between different elements. However, qualitatively, the isolation mounting components will add a component to the transfer function from the desired internal physiologic vibration sources to the output of the chestpiece that has a second order high pass shelving characteristic.

Figure 4C:
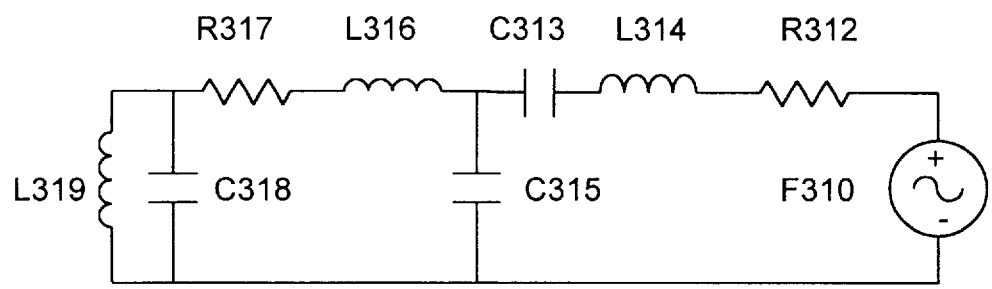
FIG. 4c shows the system of FIG. 4a where only vibration due to physiologic processes within the patient's body are considered.

Circuit 302 in FIG. 4c shows the system where only internal physiologic forces are considered. This model is obtained from the model of FIG. 4a using the principal of superposition. It can be seen that inductor 319 is now active. Inductor 319 models the mass of the chestpiece shell combined with the mass of the user' hand and arm. Inductor 319 will therefore be large compared to the other system elements, and its effects can be confined to frequencies below the audible range. Qualitatively, inductor 319 and capacitor 318 (which represents the mechanical compliance of compliant member 11) form a parallel resonant circuit. At the parallel resonance frequency, the impedance of the circuit is high, and the pressure developed across the chestpiece air cavity compliance represented by capacitor 315 will approach what would occur without any isolation mount components present. Above this parallel resonance, the system will act similar to the system described in FIG. 4b.

Figure 4D:
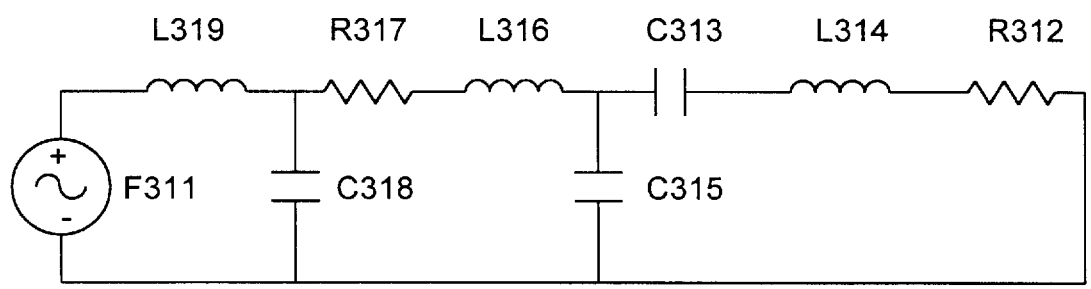
FIG. 4d shows the system of FIG. 4a where only external forces applied to the chestpiece shell are considered.

Circuit 303 in FIG. 4d shows the system when only external forces applied to the chestpiece shell are considered. This model is obtained from the model of FIG. 4a using the principal of superposition. Here it can actually be seen that there is a fourth order low pass filter transfer function from the external force source to the voltage across capacitor 315 (which is proportional to the pressure developed in the chestpiece air chamber), that acts to reduce the pressure generated in the chestpiece body air cavity due to external forces applied to the chestpiece shell. This is in contrast to the overall second order filter function that exists for the traditional stethoscope chestpiece, that was shown in FIG. 3d. This is the primary improvement generated by the preferred embodiment mechanical isolation system used in its first intended mode.

It can be seen from the above discussion that in order to minimize vibration transmission from the chestpiece shell to the chestpiece body, it will be beneficial to make the mass of the chestpiece shell 10 and chestpiece body 1 as large as is practical. It will also be beneficial to make the mechanical compliance of the compliant mount 11 as large as is practical. Making the masses and compliances large will make the resonance frequencies low, which will increase the transmission loss at frequencies above the resonance frequencies.

However, there are two potential benefits to raising the resonance frequency of the compliant member mechanical compliance and chestpiece body mass. First, raising this resonance frequency will reduce the low frequency output of the chestpiece due to internal physiologic sources. This can be beneficial when it is desired to listen to higher frequency sounds, such as respiration sounds. The reduction of low frequency energy will reduce the masking effect of the lower frequency sounds on the higher frequency sounds.

The second benefit is that the same low frequency reduction obtained for internal physiologic sounds is also obtained for external sources of vibration that couple directly into the patient's body. These types of vibrations often occur during patient transport, where vibrations from the transport vehicle cause the patient's entire body to vibrate. These types of external vibration sources are primarily low frequency, and can effectively be reduced by the isolation system of the present invention.

The desire to increase transmission loss from the chestpiece shell to the chestpiece body, and the desire to limit the low frequency output of the chestpiece due to internal and external vibration sources, place conflicting requirements on the system. However, a compromise design is possible that can effectively trade off these competing requirements. This compromise can be realized by placing the resonance of the chestpiece body mass and compliant member mechanical compliance at a first frequency, and by placing the resonance of chestpiece shell and user's hand and arm masses with the mechanical compliance of the complaint member at a second, lower frequency. This is done by making the combination of the chestpiece shell and user's hand and arm masses larger than the chestpiece body mass. An effective compromise may place the first resonance frequency of the chestpiece body mass with the compliant member mechanical compliance at a frequency in the range of 50 to 100 Hz, while the resonance of the combination of the chestpiece shell and user's hand and arm masses with the compliant member mechanical compliance is placed between 5 and 10 Hz.

In order to design such a system, the mechanical compliance of the compliant element is chosen so that it resonates with the combination of the mechanical mass of the chestpiece shell and the mechanical mass of the user's hand and arm at the first desired resonance frequency. Then, given the value of mechanical compliance chosen, the mechanical mass of the chestpiece body is calculated so that it resonates with the mechanical compliance of the compliant element at the second desired frequency. Simple mass/spring mechanical systems have a resonance frequency that can be calculated using the following formula:

$$f_s = 1/[2\pi*(M_m*C_m)^{1/2}],$$

where $f_s$ is the resonance frequency, $M_m$ is the mechanical mass and $C_m$ is the mechanical compliance.

There is another system design constraint that must be considered that will also affect the system resonance frequencies chosen. It can be seen from examining FIG. 2b that the only force available to hold chestpiece body 10 against the patient's skin 2 comes from the static deflection of compliant member 11. This will turn out to constrain the mechanical compliance of compliant member 11. A design criteria that is used in the preferred embodiment is that the static force available to hold chestpiece body 1 in place must be a minimum of five times the force exerted by gravity on chestpiece body 1. Another criteria that is also used for operation of the preferred embodiment in its first mode is that the nominal static deflection of the chestpiece shell is desired to be 1 centimeter or less.

It should be noted that the minimum static force requirement of five times the force of gravity is a rule of thumb. This criteria turns out to be a good choice for ensuring that the chestpiece body does not shift in place when held against the patient's skin. The invention is not limited in the actual static force that is used. In addition, the choice of one centimeter or less of static displacement is arbitrary. Larger or smaller displacements could easily be accommodated. All else being equal, allowing a larger static displacement will result in a larger compliance and lower system resonances. The allowable static displacement is balanced against the industrial design of the device. Allowing for larger displacements will require the size of the chestpiece assembly to increase. The rules of thumb here give a good set of trade-offs for a practical design, but it should be understood that they in no way limit the present invention.

Given the above design criteria, the mechanical compliance of the compliant member and mass of the chestpiece body can be calculated, if an assumption is made regarding the combined mass of the user's hand and arm and the chestpiece shell. Assume:

$$M_{hs}=5 kg,$$

where $M_{hs}$ is the mass of the user's hand and arm plus the mass of the chestpiece shell.

We will choose the resonance frequency of the combined mass of the user's hand and arm plus the mass of the chestpiece shell with the mechanical compliance of the compliant member to be 5 Hz. The mechanical compliance of the compliant member can then be solved for using the relationship given earlier for the calculation of a simple mass/spring resonance.

$$C_m=1/[2\ \pi^* f_o^*(M_{hs})^{1/2}]=2.206\times 10^{-4} m/N,$$

where $f_o$ is the resonance frequency of the combined mass of the user's hand and arm plus the mass of the chestpiece shell with the mechanical compliance of the compliant member. We then choose the resonance frequency of the mechanical compliance of the compliant member with the mechanical mass of the chestpiece body to be 50 Hz. The mass of the chestpiece body can be solved for using the same spring/mass resonance formula, where:

$$M_{cp}=1/[2\ \pi^* f_1^*(C_m)^{1/2}]=4.59\times 10^{-2}\ kg,$$

where $M_{cp}$ is the mass of the chestpiece body and $f_1$ is the resonance frequency of the chestpiece body mass with the compliant element mechanical compliance. The above system must be checked to ensure that sufficient static force is available to hold the chestpiece body in place against the patient's skin when the user is holds the chestpiece shell. The static force can be calculated using the following equation:

$$f_s=-(1/C_m)^* x=45.33N,$$

where $f_s$ is the static force and x is the displacement (which was given earlier as 0.01 m). This force needs to be at least a factor of five greater than the force due to gravity exerted on the chestpiece body, which is calculated below.

$$f_g=M_{cp}^*9.8m/s^2=0.449N$$

It can be seen that sufficient static force is available. It should also be noted that the ratio of mass values is proportional to the square of the ratio of resonance frequencies:

$$M_{cp}/M_{hs}=[f_o/f_1]^2$$

It should be mentioned that the static force applied was approximately a factor of 100 larger than the force due to gravity on the chestpiece body. This level of force may be excessive (it depends on the area of the skin over which this force is applied). Excessive force could modify the vibration of the skin due to internal physiologic processes in an unacceptable fashion. The amount of static force applied can be reduced without altering the associated resonance frequencies by reducing the static deflection of the compliant member.

It should also be noted that the above choices for system fundamental resonance frequencies are not unique. The invention of this disclosure is not limited in the resonance frequencies chosen.

Figure 7:
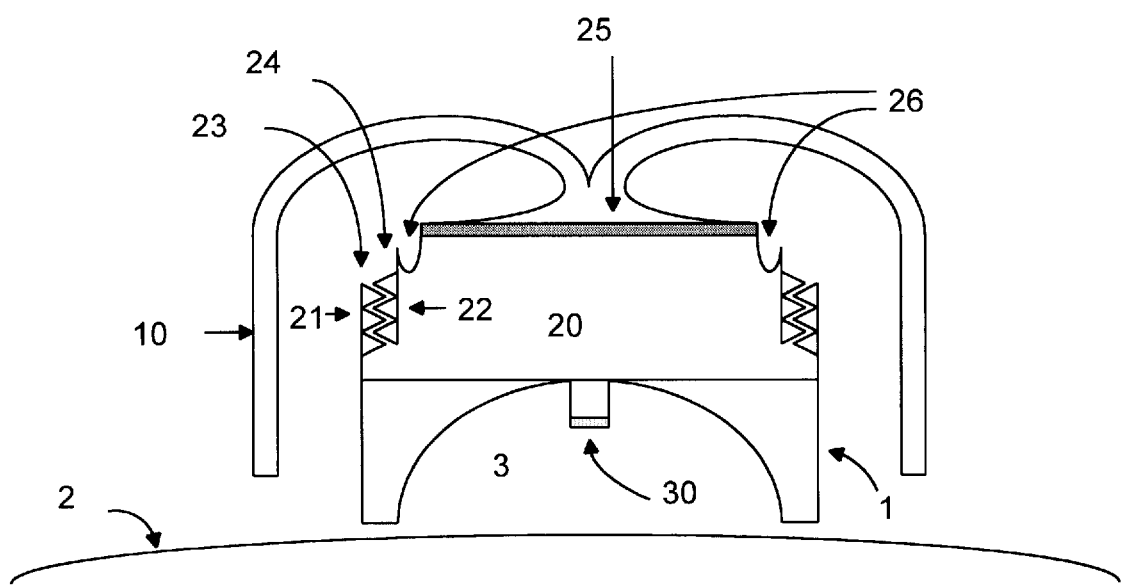
FIG. 7 shows a schematic representation of a variable compliance element that can be used to tune the isolation mounting system.

It is possible to design a system where the resonance frequencies can be varied by the user. This can be done by making the chestpiece mass user adjustable and/or making the mechanical compliance of the compliance element user adjustable. A variable mass chestpiece body can be accomplished by applying small additional weights to the chestpiece body. Methods for accomplishing this are not explicitly shown. A method for accomplishing a variable compliance element is shown in FIG. 7. It is described in more detail when operation of the isolation mount system in its second intended mode is discussed.

It was mentioned earlier that inductor 319 represented the combination of the mass of the chestpiece shell and the masses of the user's hand and arm. It will generally be the case that the user's hand and arm will have significantly higher mass than the chestpiece shell. The described behavior then will not have a great deal of dependence on the chestpiece shell mass when used in the first (and third) operating modes. This gives rise to another embodiment where a second mass is not explicitly used. The user holds the end of the compliant member that is not attached to the chestpiece body. This system will function in essentially the same manner as the system modeled in FIGS. 4a–d. Models for this new system configuration are not explicitly shown.

At higher frequencies, the lumped element electrical circuit models no longer accurately represent the system behavior. The presence of structural resonances change the behavior of the system, and the vibration reduction observed at low frequencies may no longer be present. This is the primary reason for including mechanical resistance elements 12 in the system, which are represented in FIGS. 4a–d, 5a–d, and 6a–d by resistors 317, 417, and 517. Although it is not obvious from the models, mechanical resistance elements 12 will act to damp out the effects of high frequency structural resonances in the mechanical structures of the chestpiece assembly. Specifically, mechanical resistance elements 12 will act to reduce the energy transmission at high frequencies from chestpiece shell 10 to chestpiece body 1 by damping high frequency structural resonances. This behavior provides a reduction in high frequency handling noise.

The second mode of operation of the preferred embodiment is shown in FIG. 2b. In this operating mode, the user holds chestpiece body 1, chestpiece body 1 is in contact with patient's skin 2, and chestpiece shell 10 is allowed to vibrate freely in space. Various electrical circuit models of this operating mode are shown in FIGS. 5a–d. Elements 410 through 419 in FIGS. 5a–d correspond to elements 310 through 319 in FIGS. 4a–d. The primary difference in these models as compared to the models in FIGS. 4a–d is the location of external force source 411 (for those models that show this force source). Also, since the user is holding the chestpiece body in this mode, inductor 419 now represents only the mass of the chestpiece shell, and inductor 416 represents the combination of the chestpiece body mass and the masses of the user's hand and arm.

Figure 5A:
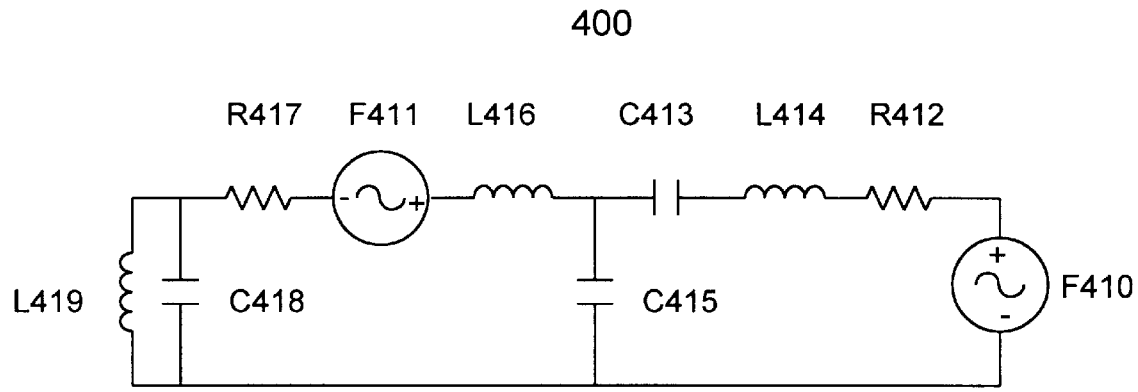
FIG. 5a is an electrical circuit model that represents the behavior of the preferred embodiment stethoscope with mechanical isolation mount system according to this invention operated in its second mode, where the user holds the chestpiece body.

Circuit 400 in FIG. 5a gives the complete model for the preferred embodiment operating in its second operating mode, which is shown in FIG. 2b. In this second operating mode, the user holds chestpiece body 1 so that chestpiece body 1 is in contact with patient's skin 2, but chestpiece shell 2 is allowed to vibrate in free space. The mechanical compliance of compliant member 11 (modeled by capacitor 418), the mass of chestpiece shell 10 (modeled by inductor 419), and mechanical resistance elements 12 (modeled by resistor 417) provide the primary vibration isolation in this mode. Inductor 419, capacitor 418, and resistor 417 form a resonant absorber. This can most easily be seen in FIG. 5d, which is a model of the operation of the new stethoscope isolation system operated in its second intended mode, where only external forces are considered. It can be seen that the voltage across capacitor 415, which is proportional to the pressure developed in the chestpiece air chamber, will have a minimum at the resonance frequency of the absorber. This implies that there is considerable transmission loss of external vibration energy between the point where external vibration is introduced into the system and the chestpiece air cavity at this resonance frequency.

Figure 5B:
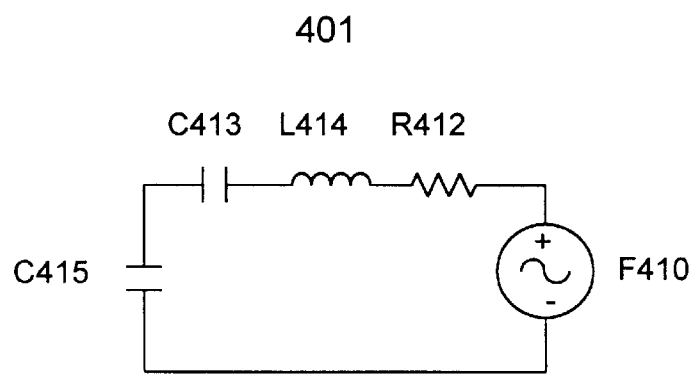
FIG. 5b shows a model of the system in FIG. 5a, where the user holds the chestpiece body against the patient's skin at zero velocity.

Circuit 401 in FIG. 5b gives the system model for the case where the user holds the chestpiece body at zero velocity. It can be seen that this model is identical to circuit 201 of FIG. 3b, which described a traditional chestpiece system where the user held the chestpiece at zero velocity. It can be seen from FIG. 5b that in this case, the rest of the isolation mount system has no effect on system behavior. There is no need for a resonant absorber if the chestpiece is held at zero velocity against the patient's skin.

Figure 5C:
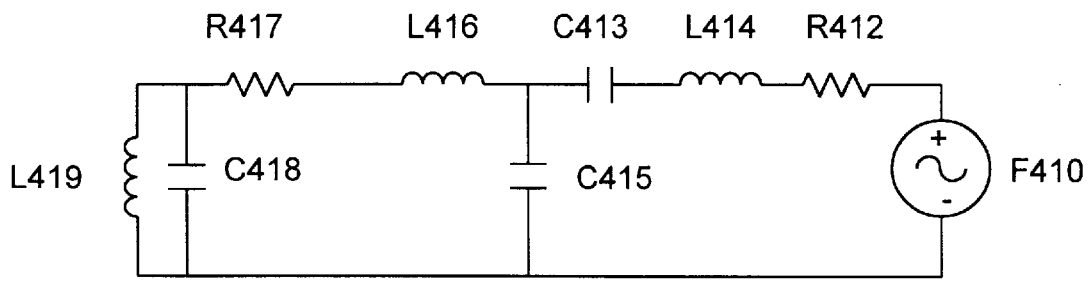
FIG. 5c shows the system of FIG. 5a where only vibration due to physiologic processes within the patient's body are considered.

The model in FIG. 5c shows the system where only effects due to internal physiologic sources are considered. This model is obtained from the model of FIG. 5a through application of the principal of superposition. Inductor 419 and capacitor 418 form a parallel resonant circuit. The impedance of this parallel resonant circuit has a maximum at the resonance frequency. At the parallel resonance frequency, the impedance approaches infinity, and the circuit path containing the parallel resonant circuit, along with inductor 416 and resistor 417 will have no effect on the system. The pressure developed in the chestpiece air chamber due to internal physiologic processes at the parallel resonance frequency will be the same as the pressure developed by a traditional stethoscope chestpiece.

It will usually be the case that the resonance frequency of the resonant absorber will be set to a low frequency, which will often be below the audible frequency range. Above the resonance frequency, the impedance of the circuit branch consisting of inductor 416, resistor 417, capacitor 418 and inductor 419 will be dominated by the impedance of inductor 416. Inductor 416 models the mass of the user's hand and arm, in addition to the mass of the chestpiece body. At higher frequencies, the above branch impedance will be large compared to the other circuit elements, and will effectively be an open circuit. The behavior of the preferred embodiment operating in its second mode, above the parallel resonance frequency of the chestpiece shell with the compliant member, will be analogous to the behavior of the traditional stethoscope modeled in FIGS. 3a–d. The conclusion to be drawn is that the resonant absorber will have a minimal effect on the pressure developed in the chestpiece air chamber due to physiologic processes within the patient's body, in the audible frequency range.

Figure 5D:
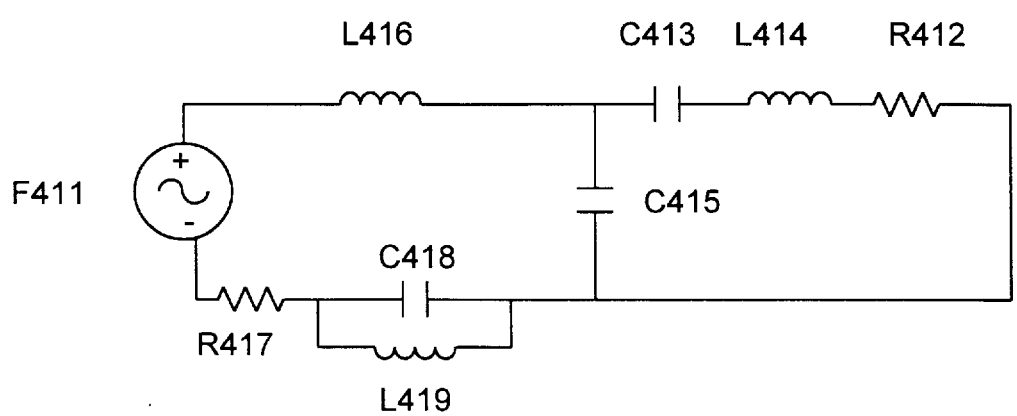
FIG. 5d shows the system of FIG. 5a where only external forces applied to the chestpiece body are considered.

The model that is of primary interest for operation of the new stethoscope isolation mount system of the current invention in its second intended mode is given by circuit 403 in FIG. 5d. FIG. 5d shows the system where only external forces applied to the chestpiece are considered. It can be seen that this system has a similar form to the system of circuit 203 in FIG. 3d, where FIG. 3d gave the model of a traditional chestpiece system where only external forces applied to the chestpiece were considered. There is one significant difference, however. An additional resonant circuit consisting of inductor 419, capacitor 418, and resistance 417 is located in the return path to force source 411.

This parallel resonant circuit represents a resonance between the mass of chestpiece shell 10, the mechanical compliance of compliant member 11, and mechanical resistance elements 12. The parallel resonant system acts as a resonant absorber. The parallel resonant circuit has an impedance maximum at the resonance frequency, and current throughout the entire circuit is reduced at this frequency. This implies that the pressure signal generated in the chestpiece air chamber due to external forces applied to the chestpiece body will also be reduced at this frequency. This is the primary benefit to operation in this second mode.

The transfer function from external force source 411 to chestpiece air chamber pressure (which is proportional to the voltage across capacitor 415) will have a bandstop characteristic (which results from the action of the resonant absorber) in addition to the second order low pass character that arises due to the action of inductor 416 and capacitor 415. This behavior should be contrasted with the fourth order low pass transfer function from external force source to chestpiece air chamber pressure obtained when the new stethoscope chestpiece isolation system is operated in its first intended mode, or the second order transfer function of a traditional stethoscope system.

Which of these first two modes is preferable in a particular situation will depend on the nature of the vibration problem encountered. The first mode applies a low pass transfer function to external vibration sources, while the second mode applies a band stop transfer function. If the external vibration source has a significant amount of broadband energy, then operation in the first mode will be preferable. If, on the other hand, the external vibration source has most of its energy confined to a small frequency band, operation in the second mode will be preferable.

An external source of vibration that has most of its energy centered in a small range of frequencies often results when an elderly individual, who suffers from a level of uncontrollable hand shaking, uses the device. The system can be tuned to the frequency of the user's hand vibration for maximum vibration reduction. The tuning can be made adjustable, to accommodate shaking frequencies that may vary between individuals. The adjustment can involve making either the mass of the chestpiece shell or the compliance of the compliant member adjustable by the user.

A system that has a variable compliant element is shown in FIG. 7. In this embodiment, the compliant element is formed by an air spring. The air spring consists of air chamber 20, piston 25, and seals 26. Piston 25 is connected to chestpiece shell 10. When chestpiece shell 10 moves relative to chestpiece body 1, piston 25 will move relative to air cavity 20. The motion of piston 25 will cause air pressure variations in air chamber 20 that will oppose the motion of piston 25. Sealed air chamber 20 acts as a spring. Seals 26 provide an air seal while allowing piston 25 to move freely.

The compliance of an air spring can be varied by adjusting the area of the piston or the volume of the cavity. In FIG. 7, the volume of air chamber 20 is made variable. Air chamber 20 is formed between upper housing 21 of chestpiece body 1 and cylindrical shell 22 (which is part of the chestpiece shell/piston assembly). The inside diameter of upper housing 21 is threaded and the outside diameter of cylindrical shell 22 is also threaded. The shell/piston assembly can be rotated with respect to the chestpiece body. Rotation of the shell/piston assembly with respect to the chestpiece body will variously increase or decrease the number of mating threads engaged in upper housing 21 and cylindrical shell 22. The volume of air chamber 20 will vary in proportion to the number of threads engaged. Variation of the volume of air chamber 20 will vary the compliance of the air spring.

A transducer 30 is shown in chestpiece air cavity 3 in FIG. 7. This transducer is responsive to the pressure in air cavity 3. The use of the variable compliant element is not, however, restricted to use with chestpieces where such a transducer is used. Any method for transducing the vibration of the patient's skin can be used with the variable compliance isolation mount system shown in FIG. 7. The invention is not restricted in the transduction method used with a variable compliance isolation mount system.

It should also be noted that the invention is not in any way limited to the use of an air spring as a variable compliant element. Any method that can be used to form a variable compliance can be adapted for use in the current invention.

There is one last point that can be made regarding operation in this second mode. In this mode, the user holds the chestpiece against the patient's skin directly. Therefore, there is no requirement for the compliant member to produce a static force to hold the chestpiece body in place. There is also no resonance of the chestpiece body with the compliant member to take into account in the design. This removes the earlier constraint on the minimum static force required, that was necessary for operation in the first mode. The removal of this constraint allows for the possibility of a much larger compliance for the compliant member. This in turn allows the mass of the chestpiece shell to be reduced for a particular desired resonance frequency. This is of practical benefit, as lower mass components can be lower cost.

The use of the preferred embodiment stethoscope with a vibration isolation mount when operated in its first two modes provides a significant advance over the performance of traditional stethoscopes, but further improvement is still possible. This further improvement can be realized by using chestpiece assembly 100 in the manner shown in FIG. 2c. FIG. 2c shows a stethoscope with the preferred embodiment mechanical isolation mount operating in its third intended mode.

In this third mode of operation, the user grasps chestpiece assembly 100 by chestpiece shell 10. The assembly is moved toward the patient so that the chestpiece body 10 comes in contact with the patients skin 2 first. The user's hand continues to move toward the patient until chestpiece shell 10 also comes in contact with patient's skin 2.

Earlier, it was shown that when the preferred embodiment is operated in its first mode, the transfer function from an external force source (which was applied to the chestpiece shell) to the chestpiece air chamber pressure output had a low pass character. At frequencies below the low pass filter cut off frequency, there is no attenuation of the force transmitted from the external source to the chestpiece body. The external force source causes a displacement of the compliant member, which in turn applies a force to the chestpiece body. This force causes a displacement of the chestpiece body relative to the patient's skin, which causes an output from the stethoscope chestpiece sensor. If external vibration energy is present at frequencies below this low frequency cutoff, it will cause an undesired output in the chestpiece.

The situation changes drastically when chestpiece shell 10 is allowed to contact patient's skin 2, as occurs when the isolation mount system is operated in its third intended mode. When chestpiece shell 10 contacts patient's skin 2, the first difference that occurs is the creation of a second transmission path for vibration energy from chestpiece shell 10 to chestpiece body 1. This second path is through the patient's skin. The effects of this second transmission path will be discussed shortly. The second change is that the patient's skin places a mechanical load on chestpiece shell 10, which directly affects the displacement of chestpiece shell 10. This turns out to dramatically change the behavior of the system.

The vibration transmission as a function of frequency for the vibration path through compliant member 11 to chestpiece body 1 from chestpiece shell 10 is essentially unchanged from operation in mode 1. The displacement of the chestpiece shell depends on the magnitude of the force applied and the mechanical load seen by the applied force. When the chestpiece shell was held in free air, this mechanical load primarily consisted of the mechanical impedance of compliant member 11. Since the isolation system is designed to keep this compliance large (small stiffness), the displacement of the chestpiece shell was large.

When chestpiece shell 10 is allowed to rest against the patient's skin 2, the displacement of the shell will be affected. The displacement of the shell again depends on the magnitude of the external force applied, and the mechanical load seen by the applied force. In mode 3 operation, the mechanical load seen by the chestpiece shell now consists of the mechanical impedance of the patient's skin, along with the mechanical impedance of the compliant member. The skin of the patient, in general, has a much larger mechanical impedance than the compliant member. When the chestpiece shell is placed against the patient's skin, the external force applied is now loaded by this larger mechanical impedance. The displacement of the shell as a result is reduced considerably.

This reduction in displacement directly reduces the force transmitted from the chestpiece shell through the compliant member to the chestpiece body. The force transmitted through the compliant member is directly proportional to the displacement of the compliant member. Since the displacement of the chestpiece shell is reduced, the displacement of the compliant member is also reduced, and the transmitted force is reduced. Essentially, the external applied force is now divided into two paths. In the first path, part of the force goes to compress the compliant member. In the second path, the rest of the force goes to compress the patient's skin.

It can clearly be seen that the force transmitted through the compliant member is significantly reduced. However, this in itself does not guarantee that the complete system provides any improvement. The transmission of vibration from the location where the chestpiece shell contacts the patient's skin to the portion of the patient's skin whose vibration is being transduced by the stethoscope chestpiece must be determined. The nature of this transfer function will determine if operation in mode 3 provides any significant benefit. As it turns out, the skin is an extremely lossy transmission path for such vibration, and the overall system performance does, in fact, improve significantly.

Figure 6A:
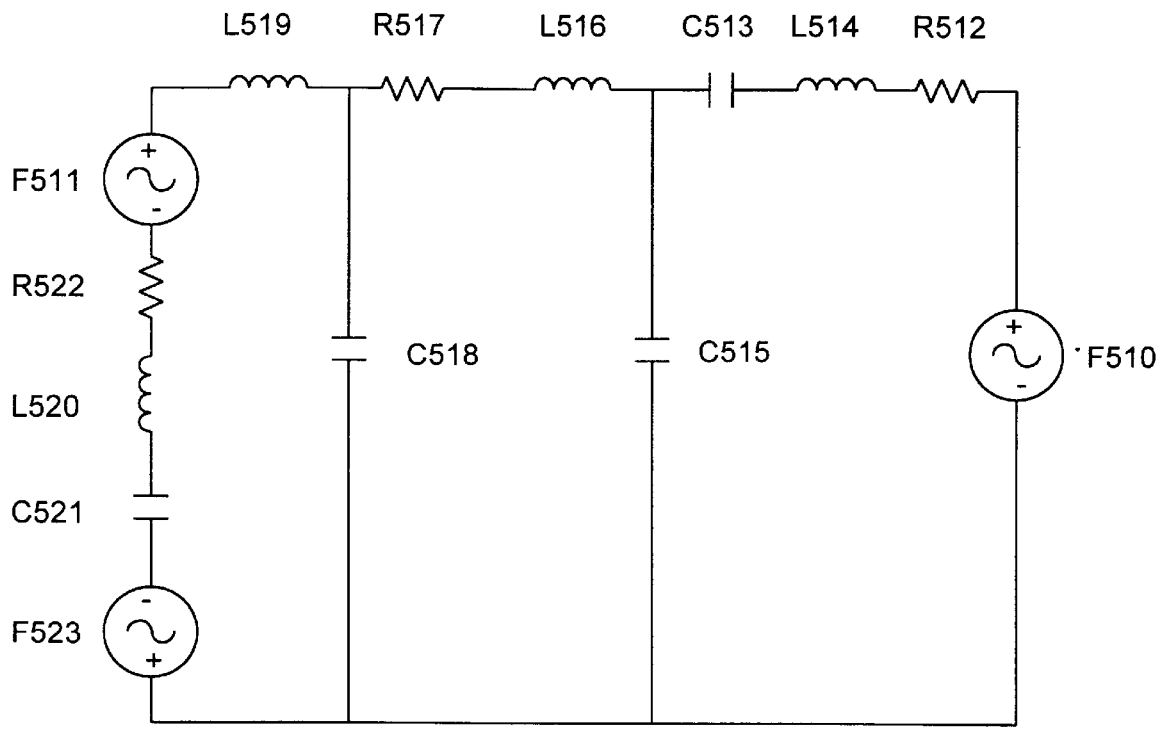
FIG. 6a is an electrical circuit model that represents the behavior of the preferred embodiment stethoscope with mechanical isolation mount system according to this invention operated in its third mode, where the user holds the chestpiece shell, and both the chestpiece body and chestpiece shell are in contact with the patient's skin.

FIGS. 6a–d show electrical circuit models of the preferred embodiment isolation system used in the third intended mode of operation. Circuit 500 in FIG. 6a shows the general model. Elements 510 through 519 are the same as elements 310 through 319 in FIGS. 4a–d. In addition, inductor 520, capacitor 521, resistor 522, and force source 523 have been added. These elements account for the chestpiece shell contacting the patient's skin. Force source 523 represents forces due to internal physiologic processes that act through the patient's skin on chestpiece shell 10. Note the polarity of force source 523. This polarity shows that this force source works in opposition to force source 510, which will reduce the total signal level available. This will be described in more detail below. Inductor 520, capacitor 521, and resistor 522 represent the mechanical load of the patient's skin at the point where the chestpiece shell contacts the patient's skin.

Figure 6B:
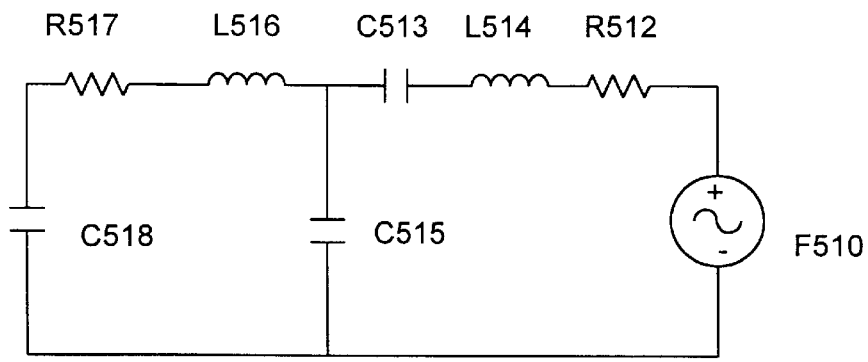
FIG. 6b shows a model of the system in FIG. 6a, where the user holds the chestpiece shell at zero velocity.

Circuit 501 in FIG. 6b shows the model of the system where the user holds the chestpiece shell at zero velocity against the patient's skin. Holding the shell at zero velocity implies that the current through inductor 519 in FIG. 6a must be zero. FIG. 6b is derived from FIG. 6a by replacing force source 511 in FIG. 6a with an open circuit. It can be seen that this circuit has exactly the same form as the circuit 301 given in FIG. 4b, and will behave identically. The addition of the isolation mount system under these conditions will add a high pass shelf response function to the transfer function from internal force sources to chestpiece output pressure.

Figure 6C:
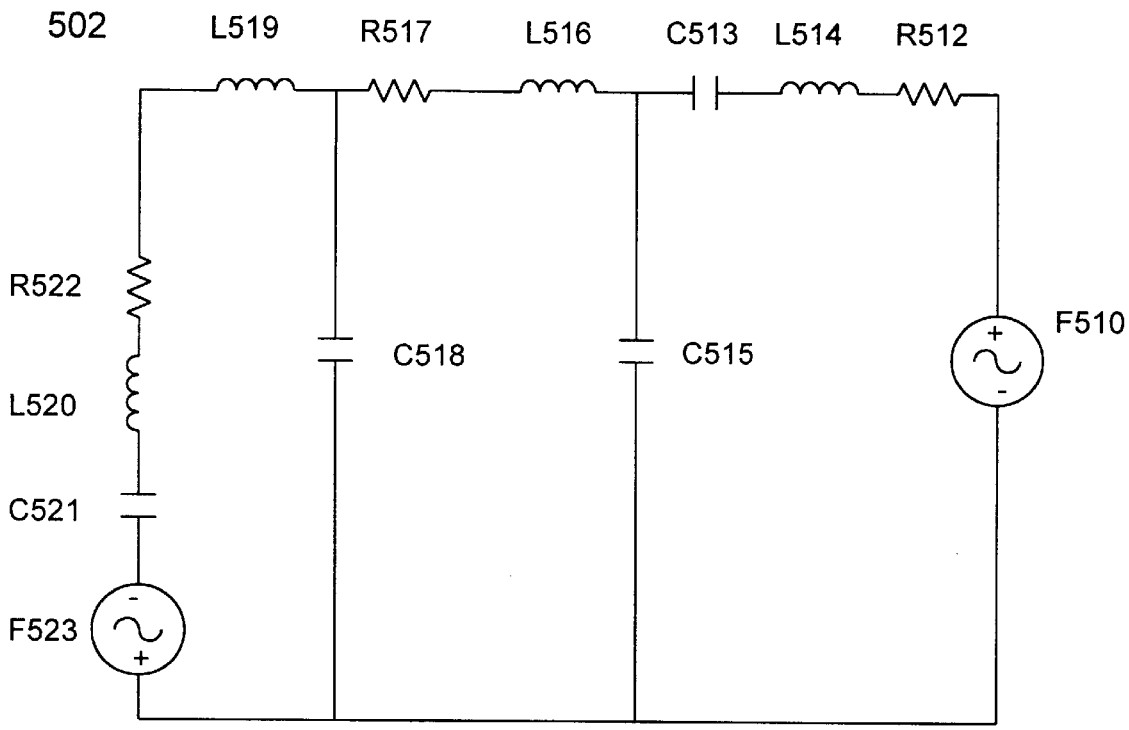
FIG. 6c shows the system of FIG. 6a where only vibration due to physiologic processes within the patient's body are considered.

Circuit 502 of FIG. 6c gives the model when only internal physiologic forces are considered. It was obtained by applying the principal of superposition to the model of FIG. 6a. Again, as in all the models given, the important variable is the voltage across capacitor 515 which is proportional to the pressure developed in the chestpiece air chamber. It can be seen that the internal force sources shown are acting with opposite polarity. Force applied through the skin to chestpiece shell 10 tries to move chestpiece shell 10 in the same direction as the skin moves under chestpiece body 1. This motion will tend to cause a reduction in the signal level developed in the chestpiece air chamber.

It can also be seen that the force applied through the skin to chestpiece shell 10 is low pass filtered by the combination of the masses of chestpiece shell 10 combined with the user's hand and arm, the mechanical compliance of compliant mount 11, and the mass of chestpiece body 1 (represented by inductor 519, capacitor 518, and inductor 516 respectively) before it can act on capacitor 515. This implies that the vibration of the skin under the chestpiece shell will only affect the stethoscope chestpiece output at or below the cutoff frequency of this low pass filter. In general, it can be stated that the effect on the chestpiece output signal due to internal force sources acting on the chestpiece shell will be minimal in the audible frequency range.

Figure 6D:
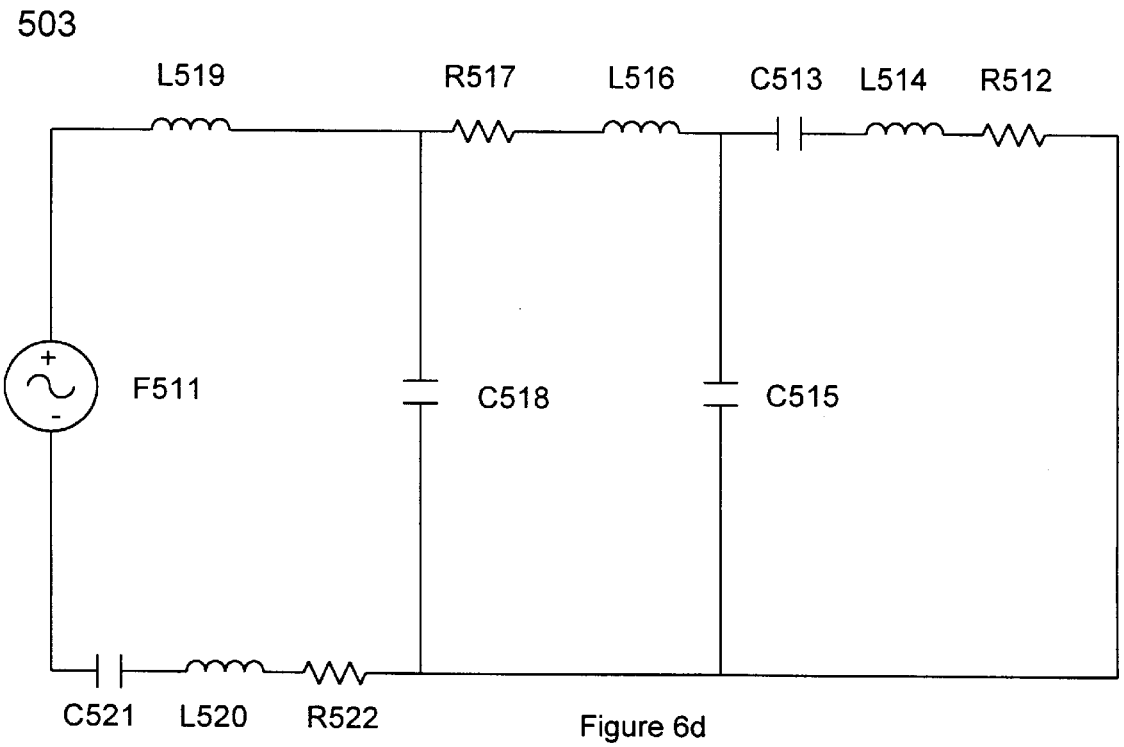
FIG. 6d shows the system of FIG. 6a where only external forces applied to the chestpiece shell are considered.

Circuit 503 of FIG. 6d shows the model when only external forces applied to chestpiece shell 10 are considered. It can be seen that this model has a large degree of similarity to the model shown in circuit 303 of FIG. 4d, which showed the preferred embodiment operating in mode 1 (where only the external force applied to chestpiece shell 10 was considered). The primary difference between the models is the inclusion of the series resonant circuit consisting of inductor 520, capacitor 521, and resistance 522, which are located in the return leg to force source 511.

The influence of this series resonant circuit can be described as follows. At the series resonance frequency, the circuit has an impedance minimum (the total series impedance is equal to the impedance of resistor 522), and a high impedance at all other frequencies. At the series resonance frequency, this system approaches the system described by the model given in FIG. 4d, where the force transmitted from the external force source to the chestpiece body has a second order low pass character, and the transfer function from external force source to chestpiece air chamber pressure has a fourth order low pass character. At all other frequencies, the impedance of the series resonant circuit increases, and the transmission of vibration energy from the external force source to the chestpiece body is reduced. This reduction is in addition to the vibration reduction of the system of FIG. 4d.

FIG. 6d shows a second order low pass filter, consisting of inductor 519 and capacitor 518 (which represent the chestpiece shell mass combined with the user's hand and arm masses, and compliant member 11 compliance), that provides transmission loss from force source 511 to the chestpiece body represented by inductor 516 (as was the case in FIG. 4d). Optimal design of this system to minimize the effects on chestpiece air chamber pressure output due to external applied forces would place the cutoff frequency for the low pass filter formed by inductor 519 and capacitor 518 below the resonance frequency of the series resonant circuit that represents the patient's skin under the chestpiece shell (modeled by inductor 520, capacitor 512, and resistor 522). In this case, there would still be significant transmission loss for vibration from the external source to the chestpiece body at the series resonance frequency of elements 522, 520, and 521 provided by the low pass filter action of inductor 519 and capacitor 518. However, if the cutoff frequency of the low pass filter were placed above the series resonance of the skin under the chestpiece shell, then there would be no transmission loss from the external force source to the chestpiece body at the skin series resonance frequency.

The models of FIGS. 6a–d do not take into account the transmission path from point of contact of the chestpiece shell with the patient's skin through the skin to the point of contact of the chestpiece body with the patient's skin. The inclusion of this transmission path in the system models adds a level of complexity that makes the underlying behavior difficult to see. Instead, the effects of this second transmission path will be discussed qualitatively.

Forces applied to chestpiece shell 10 will cause a deformation of patient's skin 2 under the point of contact of chestpiece shell 10 with patient's skin 2. The degree to which this causes an unwanted signal in the chestpiece output depends on the degree to which patient's skin 2 located under chestpiece body 1 vibrates due to the force applied to patient's skin 2 under chestpiece shell 10. It turns out that the transmission of a deformation of the skin in the plane of the skin, where the deformation is normal to the skin's surface, is extremely lossy. This implies that the transfer function that represents the transmission of vibration enrroy through the skin from the location of the chestpiece shell to the location of the chestpiece body can be made extremely lossy. If this is accomplished, there will be very little vibration energy transmitted from the point of contact of chestpiece shell 10 with the patient's skin 2 to patient's skin 2 located under chestpiece body 1.

The amount of transmission loss through the skin from one location to another depends on the mechanical impedance per unit length of the skin, and the distance between the two locations. The greater the distance, the larger the transmission loss. There is a trade off to be made here. Industrial design considerations would push for a smaller chestpiece assembly, but the improvement in transmission loss when the shell contact point is moved farther away from the chestpiece body contact point pushes for a larger chestpiece assembly. A practical minimum distance between the point of contact of the chestpiece shell and chestpiece body has been found to be 0.5". However, the invention is not in any way limited in the distance used between the points of contact with the skin of the chestpiece shell and chestpiece body. It is understood that the current invention can be used with distances greater than or less than the 0.5" mentioned above.

It is possible to construct vibration isolation systems of higher order than the second order preferred embodiment which has been described to this point. One possible higher order system can be constructed that allows a trade off to be made between the relative amounts of vibration energy transmitted through the two different paths discussed above for a chestpiece assembly used in mode 3. This can be accomplished by adding a second compliant member that is placed between the chestpiece shell and patient's skin. Adjusting the relative compliance of the second compliant member with respect to the first compliant member can allow variation of the amount of vibration energy transmitted through the two different paths. The mechanical isolation mount system now becomes third order with the addition of this second compliant element.

Many other configurations can be envisioned where additional mass, compliance, and damping elements are placed between chestpiece shell 10 and chestpiece body 1, in either series, parallel, or series-parallel configurations. Still other configurations could place additional elements between the chestpiece shell and patient's skin, and combinations of these systems could also be made. All combinations of such elements have as their basic function the isolation of the chestpiece sensor body from vibration sources other than vibration due to the internal physiologic processes within the patient's body. It is understood that the invention of this disclosure is not limited to only the isolation configurations shown. The invention of this disclosure encompasses any and all variations of mass, compliance, and damping elements that can be arranged to provide vibration isolation.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A mechanically isolated stethoscope chestpiece system, with a reduced effect of sources of vibration other than the patient internal physiological processes, comprising:

a stethoscope chestpiece which includes transducer means for transducing skin vibration, and a chestpiece body that supports such transducer means for transducing skin vibration, and that can be grasped by the user; and a spring with two ends, one end of said spring directly or indirectly coupled to the stethoscope chestpiece body, and thee other end of said spring spaced from said chestpiece body so that it may be directly or indirectly grasped by the user, for decreasing unwanted chestpiece body vibration, to reduce the effect of such vibration on the output of the chestpiece.

2. The mechanically-isolated stethoscope chestpiece system of claim 1 further including one or more mechanical resistance elements directly or indirectly coupled to the chestpiece body, to increase transmission loss of external sources of vibration between their source and the transducer means.

3. The mechanically-isolated stethoscope chestpiece system of claim 2 in which at least on e mechanical resistance element is made from elastomeric material.

4. The mechanically-isolated stethoscope chestpiece system of claim 1 further including one or more mechanical resistance elements directly or indirectly coupled to the spring, to increase transmission loss of external sources of vibration between their source and the transducer means.

5. The mechanically-isolated stethoscope chestpiece system of claim 4 in which at least one mechanical resistance element is made from elastomeric material.

6. The mechanically-isolated stethoscope chestpiece system of claim 1 further including an external mass having a mass and coupled to the spring, to assist in increasing vibration transmission loss.

7. The mechanically-isolated stethoscope chestpiece system of claim 6 in which the external mass includes a shell member surrounding the chestpiece body.

8. The mechanically-isolated stethoscope chestpiece system of claim 7 in which the chestpiece body has a front surface which is placed on a patient's skin in use, wherein the shell member is spaced back from the chestpiece body front surface sufficiently so that the shell member does not touch a flat surface when the chestpiece body front surface is placed on the flat surface, and no load is applied to the spring.

9. The mechanically-isolated stethoscope chestpiece system of claim 6 further including means for selectively coupling the external mass to the chestpiece body.

10. The mechanically-isolated stethoscope chestpiece system of claim 6 further including means for allowing the user to vary the mass of the external mass.

11. The mechanically-isolated stethoscope chestpiece system of claim 6 wherein the spring has a variable compliance, and the chestpiece system further includes means for allowing the user to vary the compliance of the spring.

12. The mechanically-isolated stethoscope chestpiece system of claim 1 further including a mass coupled to the other end of the spring, to assist in increasing vibration transmission loss.

13. The mechanically-isolated stethoscope chestpiece system of claim 1 wherein the spring has a variable compliance, and the chestpiece system further includes means for allowing the user to vary the compliance of the spring.

14. The mechanically-isolated stethoscope chestpiece system of claim 2 further including an external mass coupled to the spring, to assist in increasing vibration transmission loss.

15. The mechanically-isolated stethoscope chestpiece system of claim 4 further including an external mass coupled to the spring, to assist in increasing vibration transmission loss.

16. The mechanically-isolated stethoscope chestpiece system of claim 14 wherein the spring has a variable compliance, and the chestpiece system further includes means for allowing the user to vary the compliance of the spring.

17. The mechanically-isolated stethoscope chestpiece system of claim 15 wherein the spring has a variable compliance, and the chestpiece system further includes means for allowing the user to vary the compliance of the spring.

18. A vibration isolation system for a stethoscope chestpiece having a chestpiece body and a transducer means, comprising:

a vibration decreasing means including a spring with two ends; and means for directly or indirectly coupling one end of said spring to the chestpiece body, in which the other end of said spring is spaced from said chestpiece body so that it may be directly or indirectly grasped by the user, for decreasing unwanted chestpiece body vibration, to reduce the effect of such vibration on the output of the chestpiece.

19. The vibration isolation system for a stethoscope chestpiece of claim 18 further including one or more mechanical resistance elements directly or indirectly coupled to the chestpiece body, to increase transmission loss of external sources of vibration between their source and the transducer means.

20. The vibration isolation system for a stethoscope chestpiece of claim 18 further including one or more mechanical resistance elements directly or indirectly coupled to the spring, to increase transmission loss of external sources of vibration between their source and the transducer means.

21. The vibration isolation system for a stethoscope chestpiece of claim 18 further including an external mass having a mass and coupled to the spring, to assist in increasing vibration transmission loss.

22. The vibration isolation system for a stethoscope chestpiece of claim 21 in which the external mass includes a shell member surrounding the chestpiece body.

23. The vibration isolation system for a stethoscope chestpiece of claim 22 in which the chestpiece body has a front surface which is placed on a patient's skin in use, wherein the shell member is spaced back from the chestpiece body front surface sufficiently so that the shell member does not touch a flat surface when the chestpiece body front surface is placed on the flat surface, and no load is applied to the spring.

24. The vibration isolation system for a stethoscope chestpiece of claim 21 further including means for selectively coupling the external mass to the chestpiece body.

25. The vibration isolation system for a stethoscope chestpiece of claim 21 further including means for allowing the user to vary the mass of the external mass.

26. The vibration isolation system for a stethoscope chestpiece of claim 18 further including a mass coupled to the other end of the spring, to assist in increasing vibration transmission loss.

27. The vibration isolation system for a stethoscope chestpiece of claim 18 wherein the spring has a variable compliance, and the chestpiece system further includes means for allowing the user to vary the compliance of the spring.

28. The vibration isolation system for a stethoscope chestpiece of claim 19 further including an external mass coupled to the spring, to assist in increasing vibration transmission loss.

29. The vibration isolation system for a stethoscope chestpiece of claim 20 further including an external mass coupled to the spring, to assist in increasing vibration transmission loss.

30. The vibration isolation system for a stethoscope chestpiece of claim 21 wherein the spring has a variable compliance, and the chestpiece system further includes means for allowing the user to vary the compliance of the spring.

31. The vibration isolation system for a stethoscope chestpiece of claim 19 in which at least one mechanical resistance element is made from elastomeric material.

32. The vibration isolation system for a stethoscope chestpiece of claim 20 in which at least one mechanical resistance element is made from elastomeric material.

33. The vibration isolation system for a stethoscope chestpiece of claim 28 wherein the spring has a variable compliance, and the chestpiece system further includes means for allowing the user to vary the compliance of the spring.

34. The vibration isolation system for a stethoscope chestpiece of claim 29 wherein the spring has a variable compliance, and the chestpiece system further includes means for allowing the user to vary the compliance of the spring.

35. A vibration isolation system for a stethoscope chestpiece system, with a reduced effect of sources of vibration other than the patient internal physiologic processes, comprising:

a stethoscope chestpiece with a chestpiece body;

an external mass spaced from the chestpiece body;

a spring having two ends, one end coupled to the chestpiece body, and the other end coupled to the external mass; and one or more mechanical resistance elements directly or indirectly coupled to the chestpiece body;

wherein the spring, mass and resistance element comprise a vibration isolation system which reduces the effect of unwanted chestpiece body vibration on the chestpiece output.

36. A vibration isolation system for a stethoscope chestpiece system, with a reduced effect of sources of vibration other than the patient internal physiologic processes, comprising:

a stethoscope chestpiece with a chestpiece body;

an external mass spaced from the chestpiece body;

a spring having two ends, one end coupled to the chestpiece body, and the other end coupled to the external mass; and one or more mechanical resistance elements directly or indirectly coupled to the spring;

wherein the spring, mass and resistance element comprise a vibration isolation system which reduces the effect of unwanted chestpiece body vibration on the chestpiece output.

37. A method of using a vibration isolation system for a stethoscope chestpiece system, with a reduced effect of sources of vibration other than the patient internal physiologic processes, the chestpiece system comprising: a stethoscope chestpiece with a chestpiece body; an external mass spaced from the chestpiece body; and a spring having two ends, one end coupled to the chestpiece body, and the other end coupled to the external mass; wherein the spring and mass comprise a vibration isolation system which reduces the effect of unwanted chestpiece body vibration on the chestpiece output, the method comprising the steps of:

grasping the external mass; and placing the chestpiece body against the patient's skin.

38. The method of claim 37 further including the step of also placing the external mass against the patient's skin.

39. A method of using a vibration isolation system for a stethoscope chestpiece system, with a reduced effect of sources of vibration other than the patient internal physiologic processes, the chestpiece system comprising: a stethoscope chestpiece with a chestpiece body; an external mass spaced from the chestpiece body; and a spring having two ends, one end coupled to the chestpiece body, and the other end coupled to the external mass; wherein the spring and mass comprise a vibration isolation system which reduces the effect of unwanted chestpiece body vibration on the chestpiece output, the method comprising the steps of:

grasping the chestpiece body, leaving the external mass free; and placing the chestpiece body against the patient's skin.

* * * * *